(12) United States Patent
Oh et al.

(10) Patent No.: US 12,214,034 B2
(45) Date of Patent: *Feb. 4, 2025

(54) VACCINES AGAINST HPV AND HPV-RELATED DISEASES

(71) Applicant: BAYLOR RESEARCH INSTITUTE, Dallas, TX (US)

(72) Inventors: Sangkon Oh, Baltimore, MD (US); Sandra Zurawski, Midlothian, TX (US); Gerard Zurawski, Midlothian, TX (US)

(73) Assignee: BAYLOR RESEARCH INSTITUTE, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,696

(22) Filed: Jun. 6, 2023

(65) Prior Publication Data

US 2024/0033340 A1 Feb. 1, 2024

Related U.S. Application Data

(63) Continuation of application No. 17/194,779, filed on Mar. 8, 2021, now Pat. No. 11,717,567, which is a continuation of application No. 16/397,214, filed on Apr. 29, 2019, now Pat. No. 10,940,195, which is a continuation of application No. 15/111,357, filed as application No. PCT/US2015/011236 on Jan. 13, 2015, now Pat. No. 10,286,058.

(60) Provisional application No. 62/002,718, filed on May 23, 2014, provisional application No. 61/926,821, filed on Jan. 13, 2014.

(51) Int. Cl.
*A61K 39/12* (2006.01)
*A61K 39/395* (2006.01)
*C07K 14/005* (2006.01)
*C07K 14/025* (2006.01)
*C07K 16/28* (2006.01)
*C12N 7/00* (2006.01)
*A61K 39/00* (2006.01)

(52) U.S. Cl.
CPC ............ *A61K 39/12* (2013.01); *A61K 39/395* (2013.01); *A61K 39/39541* (2013.01); *A61K 39/3955* (2013.01); *C07K 14/005* (2013.01); *C07K 16/2878* (2013.01); *C12N 7/00* (2013.01); *A61K 2039/505* (2013.01); *A61K 2039/53* (2013.01); *A61K 2039/55511* (2013.01); *A61K 2039/585* (2013.01); *A61K 2039/6056* (2013.01); *A61K 2039/70* (2013.01); *C07K 2317/24* (2013.01); *C07K 2317/56* (2013.01); *C07K 2317/565* (2013.01); *C07K 2319/74* (2013.01); *C07K 2319/91* (2013.01); *C12N 2710/20034* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,578,770 A | 3/1986 | Mitani |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,188,837 A | 2/1993 | Domb |
| 5,254,342 A | 10/1993 | Shen et al. |
| 5,268,164 A | 12/1993 | Kozarich et al. |
| 5,271,961 A | 12/1993 | Mathiowitz et al. |
| 5,413,797 A | 5/1995 | Khan et al. |
| 5,506,206 A | 4/1996 | Kozarich et al. |
| 5,514,670 A | 5/1996 | Friedman et al. |

(Continued)

FOREIGN PATENT DOCUMENTS

| | | |
|---|---|---|
| AU | 2009/270771 | 1/2010 |
| CN | 1307484 | 8/2001 |

(Continued)

OTHER PUBLICATIONS

Attwood, "Genomics: The Babel of Bioinformatics" *Science* 2000, (290) 471-473.

(Continued)

*Primary Examiner* — Nianxiang Zou
(74) *Attorney, Agent, or Firm* — Norton Rose Fulbright US LLP

(57) ABSTRACT

Embodiments relate to novel vaccines against human papillomavirus (HPV) and HPV-related diseases, including multiple types of cancers. The HPV vaccines are composed of anti-human dendritic cell (DC) surface receptor antibodies, including CD40, and E6/7 proteins of HPV16 and 18. The technology described is not limited to making vaccines against HPV16- and HPV18-related diseases and can be applied to making vaccines carrying E6/7 from any type of HPV. The HPV vaccines described can target DCs, major and professional antigen presenting cells (APCs), and can induce and activate potent HPV E6/7-specific and strong CD4+ and CD8+ T cell responses. The HPV vaccines can be used for the prevention of HPV infection and HPV-related diseases as well as for the treatment of HPV-related diseases, including cancers.

17 Claims, 11 Drawing Sheets

Specification includes a Sequence Listing.

(56) References Cited

U.S. PATENT DOCUMENTS

| | | |
|---|---|---|
| 5,534,496 A | 7/1996 | Lee et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,770,429 A | 6/1998 | Lonberg et al. |
| 5,871,746 A | 2/1999 | Boutillon et al. |
| 6,140,059 A | 10/2000 | Shawaller |
| 6,469,143 B2 | 10/2002 | Sallberg |
| 6,541,011 B2 | 4/2003 | Punnonen et al. |
| 6,573,245 B1 | 6/2003 | Marciani |
| 7,060,495 B2 | 6/2006 | Gehrmann et al. |
| 7,067,110 B1 | 6/2006 | Gillies et al. |
| 7,118,751 B1 | 10/2006 | Ledbetter et al. |
| 7,122,187 B2 | 10/2006 | Black et al. |
| 7,261,897 B2 | 8/2007 | Skeiky et al. |
| 7,288,251 B2 | 10/2007 | Bedian et al. |
| 7,456,260 B2 | 11/2008 | Rybak et al. |
| 7,476,386 B1 | 1/2009 | Gras-Masse et al. |
| 7,560,534 B2 | 7/2009 | Deo et al. |
| 8,518,410 B2 | 8/2013 | Zurawski et al. |
| 8,961,991 B2 | 2/2015 | Zurawski et al. |
| 9,102,734 B2 | 8/2015 | Zurawski et al. |
| 9,109,011 B2 | 8/2015 | Banchereau et al. |
| 2002/0025513 A1 | 2/2002 | Sallberg |
| 2004/0001853 A1 | 1/2004 | George et al. |
| 2004/0110226 A1 | 6/2004 | Lazar et al. |
| 2004/0120948 A1 | 6/2004 | Mikayama et al. |
| 2004/0146948 A1 | 7/2004 | Britton et al. |
| 2005/0013828 A1 | 1/2005 | George et al. |
| 2005/0221295 A1 | 10/2005 | Hu et al. |
| 2006/0165690 A1 | 7/2006 | Heath et al. |
| 2006/0246089 A1 | 11/2006 | Wu et al. |
| 2007/0025982 A1 | 2/2007 | Ledbetter et al. |
| 2007/0148163 A1 | 6/2007 | Takahashi et al. |
| 2008/0181915 A1 | 7/2008 | Tripp et al. |
| 2008/0199471 A1 | 8/2008 | Bernett et al. |
| 2008/0226667 A1 | 9/2008 | Medzhitov |
| 2008/0233083 A1 | 9/2008 | Ansari et al. |
| 2008/0241139 A1 | 10/2008 | Delucia |
| 2008/0241170 A1 | 10/2008 | Zurawski et al. |
| 2008/0254026 A1 | 10/2008 | Long et al. |
| 2009/0004194 A1 | 1/2009 | Kedl |
| 2009/0068214 A1 | 3/2009 | Qian et al. |
| 2009/0238822 A1 | 9/2009 | George et al. |
| 2009/0305979 A1 | 12/2009 | Sung et al. |
| 2009/0324491 A1 | 12/2009 | Aburatani et al. |
| 2009/0324538 A1 | 12/2009 | Wong et al. |
| 2010/0135994 A1 | 6/2010 | Banchereau et al. |
| 2010/0239575 A1 | 9/2010 | Banchereau et al. |
| 2010/0291082 A1 | 11/2010 | Zurawski et al. |
| 2010/0297114 A1 | 11/2010 | Zurawski et al. |
| 2010/0322929 A1 | 12/2010 | Zurawski et al. |
| 2011/0274653 A1 | 11/2011 | Banchereau et al. |
| 2011/0311525 A1 | 12/2011 | Herbert-Fransen et al. |
| 2012/0039916 A1 | 2/2012 | Zurawski et al. |
| 2012/0231023 A1 | 9/2012 | Zurawski et al. |
| 2012/0244155 A1 | 9/2012 | Lecine et al. |
| 2012/0276148 A1 | 11/2012 | Deisseroth et al. |

FOREIGN PATENT DOCUMENTS

| | | |
|---|---|---|
| CN | 1582165 | 2/2005 |
| CN | 1198647 | 4/2005 |
| CN | 1646566 | 7/2005 |
| CN | 102770457 | 11/2012 |
| EP | 0491628 | 6/1992 |
| EP | 0239400 | 8/1994 |
| EP | 0438474 | 5/1996 |
| EP | 0463151 | 6/1996 |
| EP | 0546073 | 9/1997 |
| EP | 1391464 | 2/2004 |
| GB | 2405873 | 3/2005 |
| JP | H10/504458 | 5/1998 |
| JP | 2004/192125 | 7/2004 |
| JP | 2005/527513 | 9/2005 |
| JP | 2006/501131 | 1/2006 |
| JP | 2006/342173 | 12/2006 |
| JP | 2007/026135 | 2/2007 |
| JP | 2009/022289 | 2/2009 |
| JP | 2009/259188 | 11/2009 |
| JP | 2011-502486 | 1/2011 |
| JP | 2012-501323 | 1/2012 |
| JP | 2012/520074 | 9/2012 |
| JP | 2012-525410 | 10/2012 |
| JP | 2015/028021 | 2/2015 |
| WO | WO 88/01649 | 3/1988 |
| WO | WO 90/07861 | 7/1990 |
| WO | WO 95/06480 | 3/1995 |
| WO | WO 99/22008 | 5/1999 |
| WO | WO 99/27954 | 6/1999 |
| WO | WO 00/000156 | 1/2000 |
| WO | WO 2000/075348 | 12/2000 |
| WO | WO 2001/032714 | 5/2001 |
| WO | WO 2001/083755 | 11/2001 |
| WO | WO 2001/085798 | 11/2001 |
| WO | WO 2002/028905 | 4/2002 |
| WO | WO 2003/024480 | 3/2003 |
| WO | WO 2003/029296 | 4/2003 |
| WO | WO 2003/040169 | 5/2003 |
| WO | WO 2004/035619 | 4/2004 |
| WO | WO 2004/069873 | 8/2004 |
| WO | WO 2004/076489 | 9/2004 |
| WO | WO 2006/128103 | 11/2006 |
| WO | WO 2007/041861 | 4/2007 |
| WO | WO 2007/051169 | 5/2007 |
| WO | WO 2007/130493 | 11/2007 |
| WO | WO 2008/047723 | 4/2008 |
| WO | WO 2008/097817 | 8/2008 |
| WO | WO 2008/097870 | 8/2008 |
| WO | WO 2008/103947 | 8/2008 |
| WO | WO 2008/118587 | 10/2008 |
| WO | WO 2010/009346 | 1/2010 |
| WO | WO 2010/104747 | 9/2010 |
| WO | WO 2010/104748 | 9/2010 |
| WO | WO 2010/104749 | 9/2010 |
| WO | WO 2010/104761 | 9/2010 |
| WO | WO 2011/023785 | 3/2011 |
| WO | WO 2011/032161 | 3/2011 |
| WO | WO 2011/140255 | 11/2011 |
| WO | WO 2012/021834 | 2/2012 |
| WO | WO 2013/028996 | 2/2013 |
| WO | WO 2013/092875 | 6/2013 |
| WO | WO 2012/029802 | 10/2013 |

OTHER PUBLICATIONS

Austyn et al., "Migration Patterns of Dendritic Cells in the Mouse" *J. Exp. Med.* 1988, (167) 646-651.

Banchereau et al., "Immunobiology of Dendritic Cells" *Annu. Rev. Immunol.* 2000, (18) 767-811.

Barrios-Marrugo, Kelly, "Therapeutic Peptide-Based Vaccination Strategies Against HPV-Induced Cancers," ProQuest LLC 2012.

Bates et al., "APCs Express DCIR, a Novel C-Type Lectin Surface Receptor Containing an Immunoreceptor Tyrosine-Based Inhibitory Motif" *J. Immunol.* 1999, (163) 1973-1983.

Beauchamp et al., "A New Procedure for the Synthesis of Polyethylene Glycol-Protein Adducts; Effects on Function, Receptor Recognition, and Clearance of Superoxide Dismutase, Lactoferrin, and a2-Macroglobulin" *Analytical Biochemistry* 1983, (131) 25-33.

Benton et al., "The Use of UCOE Vectors in Combination with a Preadapted Serum Free, Suspension Cell Line Allows for Rapid Production of Large Quantities of Protein" *Cytotechnology* 2002, (38) 43-46.

Bonifaz et al., "Efficient Targeting of Protein Antigen to the Dendritic Cell Receptor DEC-205 in the Stead State Leads to Antigen Presentation on major Histocompatibility Complex Class I Products and Peripheral CD8+ T Cell Tolerance" *The Journal of Experimental Medicine* 2002, 12(196) 1627-1638.

Carlring et al., "CD40 antibody as an adjuvant induces enhanced T cell responses" *Vaccine* 2004, (22) 3323-3328.

(56) References Cited

OTHER PUBLICATIONS

Chen et al., "Enhancement and destruction of antibody function by somatic mutation: unequal occurrence is controlled by V gene combinatorial associations." *The EMBO Journal* 1995, 12(14) 2784-2794.
Colman, "Effects of amino acid sequence changes on antibody-antigen interactions" *Research in Immunology* 1994, (145) 33-36.
Connick et al., "CTL fail to accumulate at sites of HIV-1 replication in lymphoid tissue" *Journal of Immunology* 2007; (178) 3978-683.
Cruz et al., "Process development of a recombinant antibody/interleukin-2 fusion protein expressed in protein-free medium by BHK cells" *Journal of Biotechnology* 2002, 2(96) 169-183.
Dakappagari et al., "Internalizing antibodies to the C-Type lectins, L-SIGN and DC-SIGN, inhibit viral glycoprotein binding and deliver antigen to human dendritic cells for the induction of T Cell responses" *The Journal of Immunology* 2006, (176) 426-440.
Diehl et al. "CD40 activation in vivo overcomes peptide-induced peripheral cytotoxic T- lymphocyte tolerance and augments anti-tumor vaccine efficacy" *Nature Medicine* 5(7):774-779. 1999.
Durier et al., "Clinical Safety of HIV Lipopeptides used as vaccines in healthy volunteers and HIV-infected adults," *AIDS* 2006, 20(7), 1039-49.
Dye et al., "Global Burden of Tuberculosis- Estimated Incidence, Prevalence, and Mortality by Country" *JAMA* 1999, (282)677-686.
European Search Report issued in European Patent Application No EP20150735460 issued Feb. 6, 2017.
Extended European Search Report issued in U.S. Appl. No. 17/153,786, issued Jul. 26, 2017.
Finn, "Cancer Vaccines: Between the Idea and the Reality" *Nature Reviews Immunology* 2003, (3) 630-641.
Fredriksen, et al., "DNA Vaccines Increase Immunogenicity of Idiotypic Tumor Antigen by Targeting Novel Fusion Proteins to Antigen-Presenting Cells," *Molecular Therapy: The Journal of the American Society of Gene Therapy* 2006, 13(4); 776-785.
French et al., "CD40 antibody evokes a cytotoxic T-cell response that eradicates lymphoma and bypasses T-cell help" *Nature Medicine* 1999, 5(5) 548-553.
Gallo, R., "The end or the beginning of the drive to an HIV-preventative vaccine: a view from over 20 years" *The Lancet* 2005; (366) 1894-1898.
Grossman et al., "Enhancement of the Priming Efficacy of DNA Vaccines Encoding Dendritic Cell-Targeted Antigens by Synergistic Toll-Like Receptor Ligands" *BMC Immunology* 2009, 10:43 1-10.
Harper et al., "Review of Gardasil" *J Vaccines & Vaccination* 2010, 1(107), 7 pages.
Hougardy et al., "Heparin-Binding-Hemagglutinin-Induced IFN-y Release as a Diagnostic Tool for Latent Tuberculosis" *PLOS One* 2007, 10 8 pages.
Hung et al., "Therapeutic human papillomavirus vaccines: current clinical trials and future direction," *Expert Opin Biol Ther*, 8(4): pp. 421-439, 2008.
Ihara, "Human Papillomavirus and Cervical Cancer—From Molecular Biology of HPV to HPV Vaccination," *Modem Media* 2007, 53(5); 115-121.
International Search Report and Written Opinion for PCT/US2010/026375 prepared by Korean Intellectual Property Office, dated Nov. 19, 2010.
International Search Report and Written Opinion for PCT/US2010/026268 prepared by Korean Intellectual Property Office, dated Dec. 31, 2010.
International Search Report and Written Opinion for PCT/US2010/026273 prepared by Korean Intellectual Property Office, dated Jan. 9, 2011.
International Search Report and Written Opinion for PCT/US2010/026275 prepared by Korean Intellectual Property Office, dated Jan. 7, 2011.
International Search Report and Written Opinion Issued in International Application No. PCT/US2015/011236, dated Apr. 6, 2015.
International Search Report for PCT/US2012/030593, dated May 28, 2012.
Keler et al., "Antibody-targeted vaccines" *Oncogene* 2007, 26(25) 3758-3767.
Klinguer et al., "Characterization of a multi-lipopeptides mixture used as an HIV-I vaccine candidate" *Vaccine* 2000, (18) 259-267.
Kussie et al., "A single engineered amino acid substitution changes antibody fine specificity." *J. Immunol* 1994, (152) 146-152.
Langer, "Polymer-Controlled Drug Delivery Systems" *Ace. Chern. Res.* 1993, (26) 537-542.
Levine, A., "Why do we not yet have a human immunodeficiency virus vaccine?" *Journal of Virology* 2008; 82(24): 11998-12000.
Li, "Synergistic Antibody Induction by Antigen-CD40 Ligand Fusion Protein as Improved Immunogen" *Immunology* 2005, (115) 215-222.
Liu et al. "Advances in peptide-based Human Papillomavirus Therapeutic Vaccines" *Current Topics in Medicinal Chemistry*, 12: pp. 1581-1592, 2012.
Lo-Man et al., "Anti-tumor immunity provided by a synthetic multiple antigenic glycopeptide displaying a Tri-Tn glycotope" *The Journal of Immunology* 2001, (166) 2849-2854.
Mariani et al., "HPV vaccine: an overview of immune response, clinical protection, and new approaches for the future" *Journal of Translational Medicine* 2010, 8:105 1-8.
Melero et al., "Immunostimulatory monoclonal antibodies for cancer therapy," *Nat. Rev. Cancer* 2007; (7) 95-106.
Nonn et al. "Dendritic cell-based tumor vaccine for cervical cancer I: in vitro stimulation with recombinant protein-pulsed dendritic cells induces specific T cells to HPV16 E7 or HPV18 E7" *J Cancer Res Clin Oncol* 129, 511-520, 2003.
Office Action issued in corresponding Canadian Patent Application No. 2,754,743, dated Jan. 10, 2018.
Office Action Issued in Corresponding Chinese Application No. 2016100873149, dated Feb. 11, 2019.
Office Action issued in corresponding Chinese patent application No. 201580013480, dated Apr. 2, 2019 (No translation available).
Office Action Issued in Corresponding European Application No. 17153786.3, dated Aug. 17, 2018.
Office Action issued in Japanese Application No. 2016-198376, mailed Aug. 3, 2017.
Office Action Issued in Japanese Application No. 2017-007783, mailed Nov. 20, 2018.
Paquette et al., "Interferon-alpha induces dendritic cell differentiation of CML mononuclear cells in vitro and in vivo" *Leukemia* 2002, (16) 1484-1489.
Reddy et al., "Elimination of Fc Receptor-Dependent Effector Functions of a Modified lgG4 Monoclonal Antibody to Human CD4" *The Journal of Immunology* 2000, (164) 1925-1933.
Rescigno et al., "Bacteria-induced neo-biosynthesis, stabilization, and surface expression of functional class 1 molecules in mouse dendritic cells" *Proc. Natl. Acad. Sci.* 1998, (95) 5229-5234.
Rudikoff et al., "Single amino acid substitution altering antigen-binding specificity" *Proc. Nat. Acad. Sci. USA* 1982, (79) 1979-1983.
Schjetne et al., "Delivery of Antigen to CD40 Induces Protective Immune Responses against Tumors" *The Journal of Immunology* 2007, 178(7) 4169-4176.
Schuurhuis et al., "Immature Dendritic Cells Acquire CDS+ Cytotoxic T Lymphocyte Priming Capacity upon Activation by T Helper Cell-independent of -dependent Stimuli" *J. Exp. Med.* 2000, (192) 145-150.
Search Report Issued in Corresponding Chinese Application No. 2016100873149, dated Jan. 29, 2019.
Skolnick et al., "From genes to protein structure and function: novel applications of computational approaches in the genomic era" *Trends in Biotech.* 2000, (18) 34-39.
Soares et al., "Three different vaccines based on the 140-amino acid MUC1 peptide with seven tandemly repeated tumor-specific epitopes elicit distinct immune effector mechanisms in wild-type versus MUC1-Transgenic mice with different potential for tumor rejection" *The Journal of Immunology* 2001, (166) 6555-6563.
Spitler, "Cancer Vaccines: The Interferon Analogy" *Cancer Biotherapy* 1995, (10) 1-3.
Steinman, "The Dendritic Cell System and its Role in Immunogenicity" *Annual Review Immunology* 1991, (9) 271-296.

(56) References Cited

OTHER PUBLICATIONS

Stork et al., "N-Glycosylation as Novel Strategy to Improve Pharmacokinetic Properties of Bispecific Single-chain Diabodies" 2008, 12(283) 7804-7812.

Tacken et al., "Dendritic-cell immunotherapy: from ex vivo loading to in vivo targeting" *Nature Reviews* 2007, 10(7) 790-802.

Trumpfheller et al., "Intensified and protective CD4+ T cell immunity in mice with anti-dendritic cell HIV gag fusion antibody vaccine" *The Journal of Experimental Medicine* 2006, 3(203) 607-617.

Van Vliet et al., "Dendritic Cells and C-Type Lectin Receptors: Coupling Innate to Adaptive Immune Responses" *Immunology and Cell Biology* 2008, (86) 580-587.

Vonderhelde et al., "Agonistic CD40 antibodies and cancer therapy" *Clin Cancer Res* 2013, (19) 1035-1043.

Walker et al. "Toward an AIDS vaccine" *Science*, 2008; (320) 760-764.

Wells et al., "Combined Triggering of Dendritic Cell Receptors Results in Synergistic Activation and Potent Cytotoxic Immunity," *J. Immunol.* 2008; (181) 3422-3431.

Winter et al., "Antibody-based therapy" *Immunology Today* 1993, 6(14).

Xiang et al., "A Dual-Function DNA Vaccine Encoding Carcinoembryonic Antigen and CD40 Ligand Trimer Induces T Cell-Mediated Protective Immunity Against Colon Cancer in Carcinoembryonic Antigen-Transgenic Mice," *J. Immunol.* 2001; (167); pp. 4560-4565.

Xiong et al., "Expression of B-Cell Naturation Antigen mRNA in Peripheral Blood Mononuclear Cells in Patients with Systemic Lupus Erythematosus" *Huaxi Yixue* 2010, 1 page (Abstract Only).

Zhang et al., "An Adenoviral Vector Cancer Vaccine that Delivers a Tumor-Associated Antigen/CD40-Ligand Fusion Protein to Dendritic Cells" *PNAS* 2003, 25(100) 15101-15106.

VACCINES AGAINST HPV AND HPV-RELATED DISEASES

This application is a continuation of U.S. patent application Ser. No. 17/194,779, filed Mar. 8, 2021, which is continuation of U.S. patent application Ser. No. 16/397,214, filed Apr. 29, 2019, now issued U.S. Pat. No. 10,940,195, issued Mar. 9, 2021, which is a continuation of U.S. patent application Ser. No. 15/111,357, filed Jul. 13, 2016, now issued U.S. Pat. No. 10,286,058, issued May 14, 2019, which is a national phase application under 35 U.S.C. § 371 of International Application No. PCT/US2015/011236, filed Jan. 13, 2015, which claims the benefit of priority to U.S. Provisional Patent Application Ser. No. 61/926,821, filed Jan. 13, 2014, and U.S. Provisional Patent Application Ser. No. 62/002,718, filed May 23, 2014, the entire contents of each of which are hereby incorporated by reference in their entirety.

The invention was made with government support under Grant No. U19 AI057234 awarded by the National Institutes of Health and the National Institute of Allergy and Infectious Diseases. The government has certain rights in the invention.

BACKGROUND OF THE INVENTION

The application contains a Sequence Listing prepared in compliance with ST.26 format and is hereby incorporated by reference in its entirety. Said Sequence Listing, created on Oct. 13, 2023 is named "BHCSP0404USC3V2" and is 41,134 bytes in size.

1. Field of the Invention

The present invention relates generally to the field of medicine. More particularly, it concerns new and novel vaccines against Human Papilloma Virus (HPV) and HPV-related diseases, including multiple types of cancers.

2. Description of Related Art

Human papillomavirus (HPV) is one of the most common sexually-transmitted pathogens. Current HPV prophylactic vaccine have shown significant clinical efficacy in the prevention of HPV infection, but it exhibits no efficacy in the treatment of infected patients and HPV-related cancers. HPV infection causes virtually all cervical cancers, and many anal, vaginal, vulvar, penile, and oropharyngeal (throat) cancers. Thus, the development of safe and effective vaccines for patients who are infected with HPV and have HPV-related cancers are in high demand HPV infection also causes HIV-related malignancy and cancers.

Current HPV vaccines are recombinant virus-like particles made of capsid (L1) proteins of HPV 6, 11, 16, and 18. These vaccines can elicit strong antibody responses and thus can prevent HPV infection. To suppress viral replication and to eradicate HPV-related cancers, vaccines need to evoke strong T cell responses, particularly cytotoxic CD8+ lymphocytes (CTLs) that can kill virus-infected cells followed by the inhibition of HPV replication as well as HPV-related tumor cells.

Several types of vaccine models (including peptides, proteins, and DNA-based vaccines and vaccines carried by live-attenuated vectors) have been tested, but these vaccines have drawbacks either in efficacy or safety particularly in immunodeficient patients. This gap necessitates developing safe and potent immunotherapeutic vaccines against HPV-associated cancer.

A wealth of evidence has led to the conclusion that virtually all cases of cervical cancer are attributable to persistent infection by a subset of HPV types, especially HPV type 16 (HPV 16) and HPV type 18 (HPV 18). These HPV types also cause a proportion of other cancers of mucosa, including vulvar, vaginal, anal, penile, and oropharyngeal cancers. HPV 16 is the predominant type in squamous cell carcinoma of the cervix, and HPV 18 is the second most common type with prevalence ranging from 12.6% in Central/South America to 25.7% in South Asia. In addition, HPV 18 has been implicated in rapidly developing and potentially more aggressive cervical carcinomas. However, subclinical infections are the most common manifestation of HPV infection. Different studies reported between 15% and 36% of subclinical infections in sexually active adults.

SUMMARY OF THE INVENTION

Disclosed is a fusion protein comprising an anti-CD40 antibody or fragment thereof, comprising at least three complementarity determining regions from an anti-CD40 antibody, at least one peptide linker, and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises at least the variable region from an anti-CD40 antibody. The variable region can be from a light chain or heavy chain. In some embodiments, the anti-CD40 antibody or fragment thereof comprises at least the variable region from an anti-CD40 antibody light chain and at least the variable region from an anti-CD40 antibody heavy chain. In some embodiments, the anti-CD40 antibody or fragment thereof comprises six CDRs from an anti-CD40 antibody. In some embodiments, the anti-CD40 antibody or fragment thereof is humanized. In some embodiments, the peptide linker or linkers are a flexible linker. In some embodiments, the peptide linker or linkers comprise one or more glycosylation sites. In some embodiments, the peptide linker or linkers are Flexv1 (SEQ ID NO:5) and/or f1 (SEQ ID NO:6). In some embodiments, the HPV antigens are E6 and E7. In some embodiments, the fusion protein comprises the sequence of SEQ ID NO:19. In some embodiments, the fusion protein comprises the sequence of SEQ ID NO:21. In some embodiments, at least one HPV E6 antigen is an HPV type 16 antigen and at least one HPV E6 antigen is an HPV type 18 antigen. In some embodiments, at least one HPV E7 antigen is an HPV type 16 antigen and at least one HPV E7 antigen is an HPV type 18 antigen. In some embodiments, at least one HPV E6 antigen is an HPV type 16 antigen and at least one HPV E6 antigen is an HPV type 18 antigen and at least one HPV E7 antigen is an HPV type 16 antigen and at least one HPV E7 antigen is an HPV type 18 antigen.

Also disclosed is a fusion protein comprising the amino acid sequences of at least SEQ ID NOs:11-13 or SEQ ID NOs:14-16 and at least one human papillomavirus (HPV) E6 or E7 antigen. In some embodiments, the fusion protein comprises SEQ ID NOs:11-13 and SEQ ID NOs:14-16. In some embodiments, the E6 or E7 antigen or antigens are HPV type 16 or HPV type 18 antigens. In some embodiments, the fusion protein further comprises a peptide linker. In some embodiments, the peptide linker is a flexible linker. In some embodiments, the peptide linker comprises one or more glycosylation sites. In some embodiments, the peptide linker is Flexv1 (SEQ ID NO:5) and/or f1 (SEQ ID NO:6).

Also disclosed is a pharmaceutical composition comprising any of the above fusion proteins.

Also disclosed is a method of making any of the above fusion proteins comprising isolating the fusion protein from a recombinant host cell expressing the fusion protein.

Also disclosed is a composition comprising a dendritic cell targeting complex comprising an anti-CD40 antibody or fragment thereof comprising at least three complementarity determining regions from an anti-CD40 antibody, at least one peptide linker and at least one human papillomavirus (HPV) E6 or E7 antigen, wherein the E6 or E7 antigen or antigens are an HPV type 16 or HPV type 18 antigen. In some embodiments, the anti-CD40 antibody or fragment thereof comprises at least the variable region from an anti-CD40 antibody. The variable region can be from a light chain or heavy chain. In some embodiments, the anti-CD40 antibody or fragment thereof comprises at least the variable region from an anti-CD40 antibody light chain and at least the variable region from an anti-CD40 antibody heavy chain. In some embodiments, the anti-CD40 antibody or fragment thereof comprises six CDRs from an anti-CD40 antibody. In some embodiments, the anti-CD40 antibody or fragment thereof is humanized. In some embodiments, the peptide linker or linkers are a flexible linker. In some embodiments, the peptide linker or linkers comprise one or more glycosylation sites. In some embodiments, the peptide linker or linkers are selected from Flexv1 (SEQ ID NO:5) or f1 (SEQ ID NO:6). In some embodiments, the HPV antigens are E6 and E7. In some embodiments, the fusion protein comprises the sequence of SEQ ID NO:19. In some embodiments, the fusion protein comprises the sequence of SEQ ID NO:21. In some embodiments, at least one HPV E6 antigen is an HPV type 16 antigen and at least one HPV E6 antigen is an HPV type 18 antigen. In some embodiments, at least one HPV E7 antigen is an HPV type 16 antigen and at least one HPV E7 antigen is an HPV type 18 antigen. In some embodiments, at least one HPV E6 antigen is an HPV type 16 antigen and at least one HPV E6 antigen is an HPV type 18 antigen and at least one HPV E7 antigen is an HPV type 16 antigen and at least one HPV E7 antigen is an HPV type 18 antigen.

In some embodiments the HPV E6 and E7 antigens are selected from SEQ ID NO: 1-4. In other embodiments the HPV E6 and E7 antigens are at least 70%, 75%, 80%, 85%, 90%, 95%, 98%, 99% or 100%, or any range derivable therein, identical to any combination of SEQ ID NO: 1-4. In other embodiments the HPV E6 and E7 antigens are at least 70%, 75%, 80%, 85%, 90%, 95%, 98%, 99% or 100%, or any range derivable therein, identical to SEQ ID NO: 1-4. In still other embodiments, the HPV E6 antigen is a 50, 55, 60, 65, 70, 75, 80, 85, 90, 100, 105, 110, 115 or 120, or any range derivable therein, subset of contiguous amino acids of SEQ ID NO: 1 and/or 3 and the HPV E7 antigen is a 50, 55, 60, 65, 70, 75, 80, 85, 90, 95, 100, 105, 110, 115 or 120, or any range derivable therein, subset of contiguous amino acids of SEQ ID NO: 2 and/or 4.

Also disclosed is a vector comprising a polynucleotide sequence encoding a fusion protein comprising an anti-CD40 antibody or fragment thereof comprising at least three complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region. In some embodiments, the anti-CD40 antibody or fragment thereof comprises an anti-CD40 antibody heavy chain variable region. In some embodiments, the polynucleotide sequence encodes at least one HPV type 16 E6 antigen, at least one HPV type 16 E7 antigen or at least one HPV type 18 E6 antigen and at least one HPV type 18 E7 antigen. In some embodiments, the polynucleotide sequence encodes a polypeptide comprising SEQ ID NO: 19. In some embodiments, the polynucleotide sequence encodes a polypeptide comprising SEQ ID NO: 21. In some embodiments, the polynucleotide sequence encodes at least one HPV type 16 E6 antigen, at least one HPV type 16 E7 antigen, at least one HPV type 18 E6 antigen and at least one HPV type 18 E7 antigen.

Also disclosed is a method for preventing a human papillomavirus (HPV) infection comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, dendritic cell targeting complex comprises SEQ ID NO: 21. In some embodiments, the composition further comprises an adjuvant. In some embodiments, the method further comprises administering to the patient a separate HPV vaccine. In some embodiments, the separate HPV vaccine is Gardasil™ or Cervarix™.

Also disclosed is a method for treating a human papillomavirus (HPV) infection comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO:

21. In some embodiments, the method further comprises administering to the patient a separate HPV treatment.

Also disclosed is a method for inducing an immune response to at least one HPV epitope comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the composition further comprises an adjuvant. In some embodiments, the method further comprises administering to the patient a separate HPV vaccine. In some embodiments, the separate HPV vaccine is Gardasil™ or Cervarix™.

Also disclosed is a method for potentiating an immune response to at least one HPV epitope comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, potentiating an immune response is directed towards potentiating or increasing or enhancing memory T-cells. In some embodiments, the method further comprises administering to the patient a separate HPV treatment.

Also disclosed is a method for preventing a human papillomavirus (HPV) related disease comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the composition further comprises an adjuvant. In some embodiments, the HPV related disease is dysplasia, benign neoplasia, pre-malignant neoplasia or cancer. In some embodiments, the HPV related disease is cancer. In some embodiments, the cancer is cancer of the cervix, vulva, vagina, penis, anus, oropharynx, throat or lung. In some embodiments, the method further comprises administering to the patient a separate HPV vaccine. In some embodiments, the separate HPV vaccine is Gardasil™ or Cervarix™.

Also disclosed is a method for treating a human papillomavirus (HPV) related disease comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the HPV related disease is dysplasia, benign neoplasia, pre-malignant neoplasia or cancer. In some embodiments, the HPV related disease is cancer. In some embodiments, the cancer is cancer of the cervix, vulva, vagina, penis, anus, oropharynx, throat or lung. In yet further embodiments, the cancer is head and neck cancer. In some embodiments, the method further comprises administering to the patient a separate treatment. In some embodiments, the method further comprises administering to the patient a cancer treatment.

Also disclosed is a method of inhibiting HPV-infected cells in a patient comprising administering to the patient an effective amount of a composition comprising any of the above fusion proteins or vectors. In some embodiments, the HPV-infected cells are in a tumor.

Also disclosed is a method of reducing the size or mass of a tumor in a patient that is suffering from an HPV infection or the tumor comprises HPV-infected cells, comprising administering to the patient an effective amount of a composition comprising any of the above fusion proteins or vectors. The percent reduction in size or mass of the tumor or the percent regression of the tumor during or following treatment may be at least 10%, 20%, 25%, 30%, 35%, 40%, 45%, 50%, 55%, 60%, 65%, 70% 75%, 80%, 85%, 90%, 95% to 100% or any derivable range therein. The percent reduction in size or mass of the tumor or the percent regression of the tumor may be such that the tumor size eases discomfort and improves the patient's quality of life or leads to, or is associated with, a clinically favorable outcome.

Disclosed is a method of extending survival or a patient or subject suffering from an HPV related disease comprising administering to a patient a composition comprising a dendritic cell targeting complex comprising an anti-CD40 antibody or fragment thereof comprising at least six complementarity determining regions from an anti-CD40 antibody, at least one peptide linker and at least one human papillomavirus (HPV) E6 or E7 antigen, wherein the E6 or E7 antigen or antigens are HPV type 16 or HPV type 18 antigens. In some embodiments, the anti-CD40 antibody or fragment thereof comprises an anti-CD40 antibody light chain variable region and an anti-CD40 antibody heavy chain variable region. In some embodiments, the anti-CD40 antibody or fragment thereof is humanized. In some embodiments, at least one HPV E6 antigen is an HPV type 16 antigen and at least one HPV E7 antigen is an HPV type 16 antigen. In some embodiments, at least one HPV E6 antigen is an HPV type 18 antigen and at least one HPV E7 antigen is an HPV type 18 antigen. In some embodiments, at least one HPV E6 antigen is an HPV type 16 antigen, at least one HPV E7 antigen is an HPV type 16 antigen, at least one HPV E6 antigen is an HPV type 18 antigen and at least one HPV E7 antigen is an HPV type 18 antigen. In some embodiments, the dendritic cell targeting complex comprises SEQ ID NO: 19. In some embodiments, the dendritic cell targeting complex comprises SEQ ID NO: 21. In some embodiments, the HPV related disease is dysplasia, benign neoplasia, pre-malignant neoplasia or cancer. In some embodiments, the HPV related disease is cancer. In some embodiments, the cancer is cancer of the cervix, vulva, vagina, penis, anus, oropharynx, throat or lung. In yet further embodiments, the cancer is head and neck cancer. In some embodiments, the method further comprises administering to the patient a separate treatment. In some embodiments, the method further comprises administering to the patient a cancer treatment. In some aspects, survival is extended by a period of 1, 2, 3, 4, 5, 6, 7, 8, 9 or 10 days, or any range derivable therein. In some aspects, survival is extended by a period of 1, 2, 3, 4, 5, 6, 7, 8, 9 or 10 weeks, or any range derivable therein. In some aspects, survival is extended by a period of 1, 2, 3, 4, 5, 6, 7, 8, 9 or 10 months, or any range derivable therein. In some aspects, survival is extended by a period of 1, 2, 3, 4, 5, 6, 7, 8, 9, 10, 11, 12, 13, 14, 15, 20, 25 or 30 years, or any range derivable therein.

Any of the methods disclosed above may be implemented using any of the fusion proteins, compositions, and/or vectors disclosed above.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 9A) Survival curves. 10 mice per group. (FIG. 9B) TC-1 tumor progression. 10 mice per group.

DESCRIPTION OF ILLUSTRATIVE EMBODIMENTS

Figure 1:
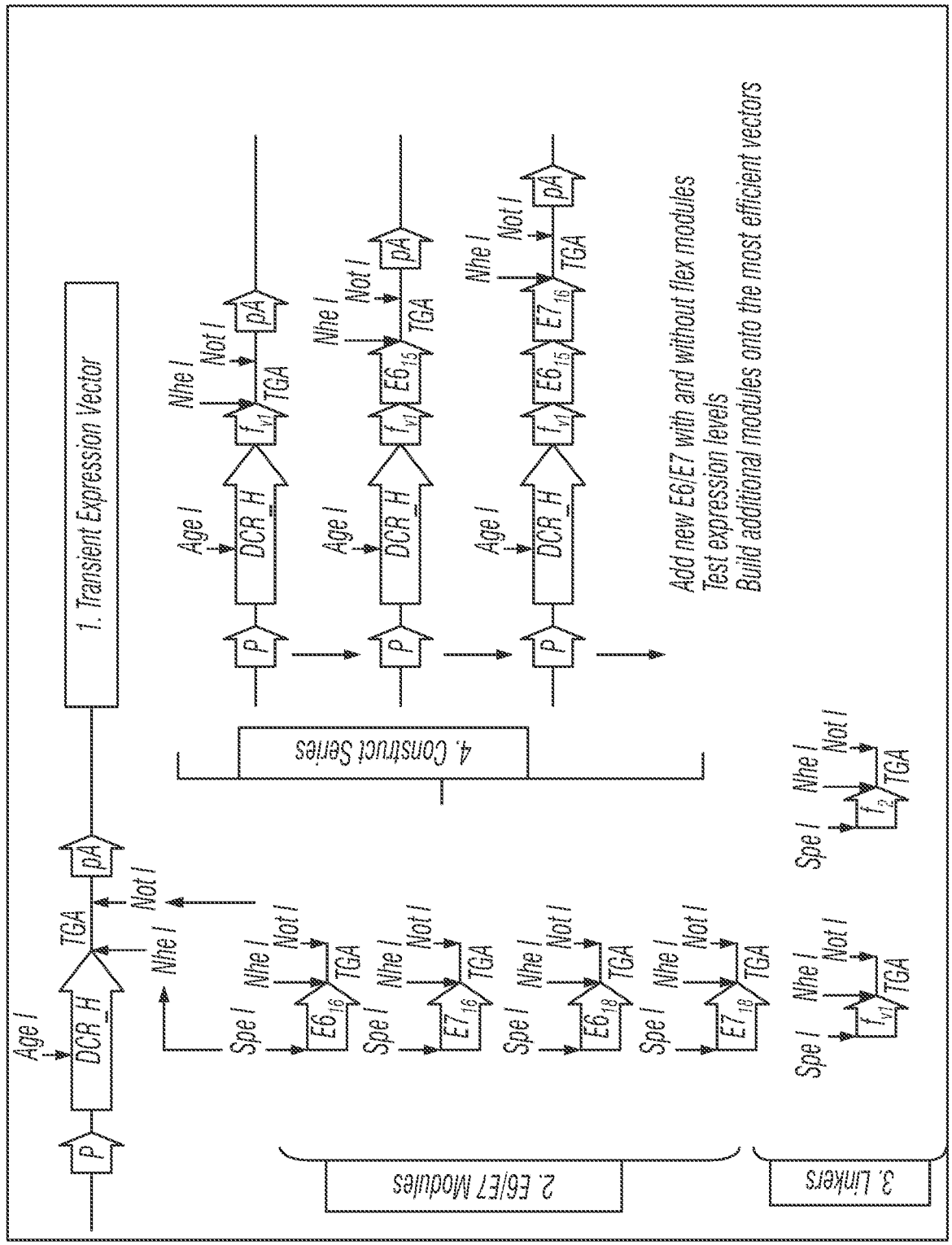
FIG. 1: Scheme for development of recombinant anti-DC receptor-E6/E7 vaccines.

As described in the Examples, an anti-CD40 antibody to which an HPV E6 and E7 antigen has been fused (called hereafter 'anti-CD40-HPV16.E6/7') has been shown to induce a strong immune response against said antigens (including a strong T-cell response). This provides an efficient and effective method of eliciting and potentiating an immune response to HPV antigens. Moreover, an anti-CD40-HPV16.E6/7 has been used in a prime-boost strategy in combination with a poly IC adjuvant to suppress TC-1 tumor progression in human CD40 transgenic mice. Thus, it has been demonstrated that said anti-CD40-HPV16.E6/7 can elicit E6/E7-specific CD8+ cytotoxic T lymphocytes and when administered with a poly IC adjuvant, serves as an efficient vaccine.

I. NUCLEIC ACIDS

In certain embodiments, there are recombinant nucleic acids encoding the proteins, polypeptides, or peptides described herein. Polynucleotides contemplated for use in methods and compositions include those encoding antibodies to DC receptors or binding portions thereof, HPV antigens, linker regions or adjuvants.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or fewer in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode polypeptides (e.g., an antibody or fragment thereof) that bind to DC receptors, are HPV antigens, are linker regions or are fusion proteins comprising any combination of a DC receptor antibody or antibodies or fragments thereof, HPV antigens (such as E6 or E7 from any HPV type) and linker regions. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody or fragment thereof that binds a dendritic cell receptor, an HPV antigen or antigens (e.g. E6 and/or E7 from one or multiple HPV types), a linker or multiple linker regions, an adjuvant or multiple adjuvants, any combination of the aforementioned proteins or a fusion protein or fusion proteins comprising any combination of the aforementioned proteins.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

II. PROTEINACEOUS COMPOSITIONS

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules or loss of antigenicity in antigenic peptides or proteins. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein (including a fusion protein) in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that binds DC receptor or a fusion protein comprising an antibody that binds a DC receptor, and may be used in combination with other HPV antigens, linker regions or adjuvants described herein.

Polypeptides and Polypeptide Production

Embodiments involve polypeptides, peptides, and proteins and immunogenic fragments thereof for use in various aspects described herein. For example, specific antibodies are assayed for or used in binding to DC receptors and presenting HPV antigens. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an DC receptor or receptor fragment comprises substantially all of the extracellular domain of a protein which has at least 85% identity, at least 90% identity, at least 95% identity, or at least 97-99% identity, including all values and ranges there between, to a sequence selected over the length of the fragment sequence.

Also included in immunogenic compositions are fusion proteins composed of HPV antigens, or immunogenic fragments of HPV antigens (e.g., E6 or E7). HPV antigens may be from any type (e.g. type 16 or type 18). For example an HPV antigen may be selected from a single or combination of HPV type. An HPV antigen or combination of HPV antigen may be from HPV type 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120. Alternatively, embodiments also include individual fusion proteins of HPV proteins or immunogenic fragments thereof or anti-DC receptor antibodies or fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

Antibodies and Antibody-Like Molecules

In certain aspects, one or more antibodies or antibody-like molecules (e.g., polypeptides comprising antibody CDR domains) may be obtained or produced which have a specificity for a DC receptor. These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprising antibody CDR domains that retain antigen binding activity. Thus, the term "antibody" is used to refer to any antibody-like molecule that has an antigen binding region, and includes antibody fragments such as Fab', Fab, F(ab')2, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region (Pack, et al., 1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al., 2003 describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate DC receptor-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as DC receptor-binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibiters of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. In order to describe antibodies of some embodiments, the strength with which an antibody molecule binds an epitope, known as affinity, can be measured. The affinity of an antibody may be determined by measuring an association constant (Ka) or dissociation constant (Kd). Antibodies deemed useful in certain embodiments may have an association constant of about, at least about, or at most about 10e6, 10e7, 10e8, 10e9 or M or any range derivable therein. Similarly, in some embodiments antibodies may have a dissociation constant of about, at least about or at most about 10e-6, 10e-7, 10e-8, 10e-9 or M or any range derivable therein. These values are reported for antibodies discussed herein and the same assay may be used to evaluate the binding properties of such antibodies In certain embodiments, a polypeptide that specifically binds to DC receptors is able to bind a DC receptor on the surface of the cells and present an HPV antigen that allows the generation of a robust immune response. Moreover, in some embodiments, the polypeptide that is used can provided protective immunity against HPV or provides a means of therapy for HPV by generating a robust immune response.

1. Methods for Generating Antibodies

Methods for generating antibodies (e.g., monoclonal antibodies and/or monoclonal antibodies) are known in the art. Briefly, a polyclonal antibody is prepared by immunizing an animal with a DC receptor polypeptide or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, poly IC, montaninde, GMCSF, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous, intratumoral and intraperitoneal. The production of antibodies may be monitored by sampling blood of the immunized animal at various points following immunization.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies. The use of rats is well known and may provide certain advantages (Goding, 1986, pp. 60 61). Mice (e.g., BALB/c mice) are routinely used and generally give a high percentage of stable fusions.

MAbs produced by either means may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

It is further contemplated that monoclonal antibodies may be further screened or optimized for properties relating to specificity, avidity, half-life, immunogenicity, binding association, binding disassociation, or overall functional properties relative to the intended treatment or protective effect. Thus, it is contemplated that monoclonal antibodies may have 1, 2, 3, 4, 5, 6, or more alterations in the amino acid sequence of 1, 2, 3, 4, 5, or 6 CDRs of monoclonal antibodies or humanized antibodies provided herein. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of antibodies may have an insertion, deletion, or substitution with a conserved or non-conserved amino acid. Such amino acids that can either be substituted or constitute the substitution are disclosed above.

In some embodiments, fragments of a whole antibody can perform the function of binding antigens. Examples of binding fragments are (i) the Fab fragment constituted with the VL, VH, CL and CH1 domains; (ii) the Fd fragment consisting of the VH and CH1 domains; (iii) the Fv fragment constituted with the VL and VH domains of a single antibody; (iv) the dAb fragment (Ward, 1989; McCafferty et al., 1990; Holt et al., 2003), which is constituted with a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988); (viii) bispecific single chain Fv dimers (PCT/US92/09965) and (ix) "diabodies", multivalent or multispecific fragments constructed by gene fusion (WO94/13804; Holliger et al., 1993). Fv, scFv or diabody molecules may be stabilized by the incorporation of disulphide bridges linking the VH and VL domains (Reiter et al., 1996). Minibodies comprising a scFv joined to a CH3 domain may also be made (Hu et al. 1996). The citations in this paragraph are all incorporated by reference.

Antibodies also include bispecific antibodies. Bispecific or bifunctional antibodies form a second generation of monoclonal antibodies in which two different variable regions are combined in the same molecule (Holliger & Winter, 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al, 1993), e.g. prepared chemically or from hybrid hybridomas, or may be any of the bispecific antibody fragments mentioned above. These antibodies can be obtained by chemical methods (Glennie et al., 1987; Repp et al., 1995) or somatic methods (Staerz & Bevan, 1986) but likewise by genetic engineering techniques which allow the heterodimerization to be forced and thus facilitate the process of purification of the antibody sought (Merchand et al., 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. The citations in this paragraph are all incorporated by reference.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against a DC receptor, then a library can be made where the other arm is varied and an antibody of appropriate specificity selected. Bispecific whole antibodies may be made by alternative engineering methods as described in Ridgeway et al., 1996), which is hereby incorporated by reference.

Antibody and Polypeptide Conjugates

Embodiments provide antibodies and antibody-like molecules against DC receptors, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity or immunostimulatory activity. Non-limiting examples of effector molecules which have been attached to antibodies include adjuvants, toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin. The following US patent applications are incorporated by reference to the extent they disclose antibodies, portions of antibodies, antigens, linkers, specific sequences of such antibodies, antigens and linkers, adjuvants, other components of a fusion protein or therapeutic composition, host cell or composition, sources of dendritic cells and culturing/activating of dendritic cells and derivatives of and from dendritic cells, and methods of use involving such fusion proteins: 12/024,036; 12/024,897; 12/025,010; 12/026,095; 12/036,138; 12/036,158; 12/504,463; 12/717,778; 12/717,789; 12/717,804; 12/718,365; 12/882,052; 12/882,052; 13/100,684; 13/208,993; 13/269,951; 13/282,112; 13/415,564; 13/424,582; 13/430,206; 13/594,397; 13/596,526; WO2010/104749; 13/465,371; 13/397,932; PCT/US13/72217; and PCT/US2013/05839.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948 (incorporated herein by reference), imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987, incorporated herein by reference). This approach has been reported to produce diagnostically and therapeutically promising antibodies which are currently in clinical evaluation.

2. Dendritic Cell Specific Antibodies

In certain aspects, antibodies used to target HPV antigens to dendritic cells are dendritic cell specific antibodies and bind dendritic cell receptors or receptors expressed by dendritic cells. Some of the antibodies that may be used for this purpose are known in the art.

In some embodiments anti-DCIR antibodies are used to target HPV antigens to dendritic cells. One example includes anti-dendritic cell immunoreceptor monoclonal antibody conjugates, wherein the conjugate comprises antigenic peptides that are loaded or chemically coupled to the antibody. Such antibodies are described in U.S. application No. 61/332,465 and are incorporated herein by reference.

In other embodiments anti-CD40 antibodies are used to target HPV antigens to dendritic cells. Compositions and methods for the expression, secretion and use of anti-CD40 antibodies as vaccines and antigen delivery vectors with one linked antigenic peptides are described in WO 2010/104761; all methods disclosed are incorporated herein by reference. In some embodiments the anti-CD40 antibody comprises the heavy chain and light chain variable region from monoclonal antibody 12E12, 11B6 or 12B4. In other embodiments the anti-CD40 antibody comprises the heavy chain and light chain CDRs from monoclonal antibody 12E12, 11B6 or 12B4.

In certain aspects anti-LOX-1 antibodies are used to target HPV antigens to dendritic cells. One example of such an antibody can be used to target the LOX-1 receptor on immune cells and increase the effectiveness of antigen presentation by LOX-1 expressing antigen presenting cells. Examples of such LOX-1 antibodies are described in WO 2008/103953, the contents of which are incorporated herein by reference.

In other aspects anti-CLEC-6 antibodies are used to target HPV antigens to dendritic cells. One example of such antibodies include anti-CLEC-6 antibodies used to increase the effectiveness of antigen presentation by CLEC-6 expressing antigen presenting cells. Such antibodies are described in WO 2008/103947, the methods and contents of which are incorporated herein by reference.

In yet other embodiments anti-Dectin-1 antibodies are used to target HPV antigens to dendritic cells. Anti-Dectin-1 antibodies that increase the effectiveness of antigen presentation by Dectin-1 expressing antigen presenting cells are described in WO 2008/118587, the contents of which are incorporated herein by reference.

In certain aspects, peptide linkers are used to link dendritic cell specific antibodies and HPV antigens to be presented. Peptide linkers may incorporate glycosylation sites or introduce secondary structure. Additionally these linkers increase the efficiency of expression or stability of the fusion protein and as a result the efficiency of antigen presentation to a dendritic cell. Such linkers may include SSVSPTTSVHPTPTSVPPTPTKSSP (SEQ ID NO: 6); PTSTPADSSTITPTATPTATPTIKG (SEQ ID NO:29); TVTPTATATPSAIVTTITPTATTKP (SEQ ID NO:30); QTPTNTISVTPTNNSTPTNNSNPKPNP (SEQ ID NO: 5); or TNGSITVAATAPTVTPTVNATPSAA (SEQ ID NO: 31). These examples and others are discussed in WO 2010/104747, the contents of which are incorporated herein by reference.

In other embodiments an immune adjuvant is directly fused to the dendritic cell specific antibody in order to enhance the efficacy of the vaccine. In certain aspects the immune adjuvant may be a toll-like receptor (TLR) agonist. TLR agonists comprise flagellins from *Salmonella enterica* or *Vibrio cholerae*. TLR agonists may be specific for certain TLR classes (i.e., TLR2, TLR5, TLR7 or TLR9 agonists) and may be presented in any combination or as any modification. Examples of such immune adjuvants are described in U.S. application Ser. Nos. 13/208,993, 13/415,564, and in WO 2012/021834, the contents of all of which are incorporated herein by reference. US Patent Publications 2012/0039,916 and 2012/023,102 are incorporated by reference to the extent they disclose different TLR agonists.

In some embodiments, the compositions and fusion proteins comprising dendritic cell antibodies and HPV antigens are used to treat HPV related diseases or an HPV related pathology. In some embodiments, an HPV related disease is dysplasia, benign neoplasia, pre-malignant neoplasia or cancer (malignant neoplasia). In some embodiments, the tissue or organ affected by dysplasia, benign neoplasia, pre-malignant neoplasia or cancer is the cervix, vulva, vagina, penis, anus, oropharynx, head and neck, throat or lung. In some specific embodiments the HPV related diseases or an HPV related pathology is cervical intraepithelial neoplasia (CIN), vulvar intraepithelial neoplasia (VIN), penile intraepithelial neoplasia (PIN), and/or anal intraepithelial neoplasia (AIN). In still other embodiments, the compositions and fusion proteins comprising dendritic cell antibodies and HPV antigens are used to treat HPV related Common warts, Plantar warts, Flat warts, Anogenital warts, Anal lesions, Genital cancers, Epidermodysplasia verruciformis, Focal epithelial hyperplasia (oral), Oral papillomas, Oropharyngeal cancer, Verrucous cyst or Laryngeal papillomatosis.

III. METHODS OF TREATMENT

As discussed above, the compositions and methods of using these compositions can treat a subject (e.g., prevent an HPV infection or HPV related disease or evoke a robust or potentiate an immune response to HPV or HPV related disease) having, suspected of having, or at risk of developing an infection or related disease, related to HPV.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a recipient patient. Treatment or therapy can be an active immune response induced by administration of immunogen or a passive therapy effected by administration of a fusion protein composition, immunogenic composition or protein composition comprising an antibody/antigen fusion protein, antibody/antigen fusion protein containing material, or primed T-cells.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein.

Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., 1994), by antigen-dependent killing (cytotoxic T lymphocyte assay, Tigges et al., 1996, incorporated by reference) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by or suspected of being caused by an HPV pathogen. In certain aspects embodiments include methods of treatment of HPV infection, such as an infection acquired from an HPV positive individual. In some embodiments, the treatment is administered in the presence of HPV antigens. Furthermore, in some examples, treatment comprises administration of other agents commonly used against viral infection.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

Combination Therapy

The compositions and related methods, particularly administration of an antibody that binds DC receptor and delivers an HPV antigen or antigens or peptide or peptides to a patient/subject, may also be used in combination with the administration of traditional antiviral therapies or anti-cancer therapies or drugs. These include, but are not limited to, entry inhibitors, CCR5 receptor antagonists, nucleoside reverse transcriptase inhibitors, nucleotide reverse transcriptase inhibitors, non-nucleoside reverse transcriptase inhibitors, protease inhibitors, integrase inhibitors and maturation inhibitors. Anti-cancer therapies include but are not limited to chemotherapy, radiotherapy or radiation therapy.

The compositions and related methods, particularly administration of an antibody that binds DC receptor and delivers an HPV antigen or antigens or peptide or peptides to a patient/subject, may also be used in combination with the administration of one or more anti-cancer drugs that include but are not limited to Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine comprising recombinant L1 protein of HPV types 16 and 18), Cetuximab, Chlorambucil, CHLORAMBUCIL-PREDNIS ONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine comprising recombinant L1 protein of HPV types 6, 11, 16, and 18), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Ibritumomab Tiuxetan, Ibrutinib, ICE, Iclusig (Ponatinib Hydrochloride), Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid) and Zytiga (Abiraterone Acetate).

The compositions and related methods, particularly administration of an antibody that binds DC receptor and delivers an HPV antigen or antigens or peptide or peptides to a patient/subject, may also be used in combination with the administration of radiation therapy that includes but is not limited to X-rays, gamma rays, and charged particles. The radiation may be delivered by a machine outside the body (external-beam radiation therapy), or it may come from radioactive material placed in the body near cancer cells (internal radiation therapy or brachytherapy). Internal radiation therapy may be systemic (e.g. radioactive iodine). External-beam radiation therapy may include, but is not limited to, 3-dimensional conformal radiation therapy (3D-CRT), Intensity-modulated radiation therapy (IMRT), Image-guided radiation therapy (IGRT), Tomotherapy, Stereotactic radiosurgery (SRS), Stereotactic body radiation therapy (SBRT), Proton therapy or other charged particle beams (e.g., electron beams). Internal radiation therapy or brachytherapy may comprise interstitial brachytherapy which uses a radiation source placed within tumor tissue and may be used to deliver a dose higher than external beam radiation while causing less damage to normal tissue. Brachytherapy may be given as a low-dose rate or high-dose rate treatment. In additional embodiments, brachytherapy may be permanent or temporary. Radiation therapy may comprise systemic radiation therapy. Systemic radiation therapy may comprise a swallowed or injected radioactive substance, that includes, but is not limited to any single, multiple or combination dose of Radioactive iodine ($^{131}$I), ibritumomab tiuxetan (Zevalin®), 131 tositumomab (Bexxar®), samarium-153-lexidronam (Quadramet®) and strontium-89 chloride (Metastron®) or any monoclonal bound to a radioactive substance. The dose of radiation according to different embodiments may be tailored to the specific disease, condition or cancered being treated. In some embodiments, the single or total dose may be 1-10 gray (Gy), 10-20 Gy, 20-40 Gy, 40-60 Gy, or 60-80 Gy, or any value or rage derivable therein. In some embodiments, radiation therapy or dose may be fractionated. In one embodiment, a total dose may be fractionated per day or per week. In certain embodiments the daily fractionated dose may be 1.8-2 Gy. It is contemplated that a total dose may be fractionated into daily or weekly doses in the range of 0.1 Gy to 10 Gy.

In one aspect, it is contemplated that a therapy is used in conjunction with antiviral or anti-cancer therapies. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In yet another aspect, a vaccine may be administered as part of a prime/boost strategy. A priming vaccine dose can be administered using a DC specific antibody fused to an HPV antigen in any of the embodiments described herein. A vaccine boost can be administered through the use of a second vaccine, either of the same type or from a different type of vaccine. Examples of a separate HPV vaccine include Gardasil™ (recombinant HPV quadrivalent vaccine comprising recombinant L1 protein of HPV types 6, 11, 16, and 18) or Cervarix™ (recombinant HPV bivalent vaccine comprising recombinant L1 protein of HPV types 16 and 18). Additional examples of such different vaccines include naked DNA vaccines or a recombinant viruses. The second vaccine may comprise additional HPV antigens apart from the E6 or E7 antigens that may be used in the first vaccine. It is also contemplated that the second vaccine may comprise an HPV protein such as an E6 or E7 protein plus an adjuvant either directly linked or administered independently.

Various combinations of therapy may be employed, for example antiviral or anti-cancer therapy is "A" and an antibody vaccine that comprises an antibody that binds a DC receptor and delivers an HPV antigen or a peptide or consensus peptide thereof is "B":

| |
|---|
| A/B/A B/A/B B/B/A A/A/B A/B/B B/A/A A/B/B/B B/A/B/B |
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

General Pharmaceutical Compositions

In some embodiments, pharmaceutical compositions are administered to a subject. Different aspects may involve administering an effective amount of a composition to a subject. In some embodiments, an antibody that binds DC receptor and delivers an HPV antigen or a peptide or consensus peptide thereof may be administered to the patient to protect against or treat infection by one or more HPV types or protect or treat against one or more HPV related diseases such as cancer. Alternatively, an expression vector encoding one or more such antibodies or polypeptides or peptides may be given to a patient as a preventative treatment. Additionally, such compositions can be administered in combination with an antibiotic, antiviral or anticancer agent. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the mucosal, intravenous, intramuscular, sub-cutaneous, intratumoral or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intratumoral, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1— Recombinant Fusion Proteins of Anti-DC Receptors (DCRs) and HPV E6 and E6 Fusion Proteins The inventors' scheme for the development of expression constructs for production of anti-DC receptor antibodies fused to E6 and E7 sequences from HPV 16 and 18 is given in FIG. 1. The scheme identifies an order of antigen cassettes encoding E6 and E7 from HPV 16 and 18 that is efficiently secreted and are intact when fused to the H chain C-terminus. There are 64 possible combinations of just these 4 sequences, and very many more when interspersed with flexible linker sequences. The inventors' strategy is a stepwise approach starting with each antigen alone, with and without a preceding flexible linker [8 initial constructs], then selecting those vectors that express most efficiently for adding on additional cassettes. Each cycle of construction and testing takes one week. Establishing the final production CHO-S cell lines take a further 8 weeks, including scale-up to levels suitable for vaccine production to preclinical studies in human in vitro and animal in vivo.

A transient expression vector encoding the antibody heavy chain has an in-frame Nhe I site at the C-terminus and antigen or flexible linker encoding Spe I— Not I cassettes are inserted between the vector Nhe I and Not I sites. The vector Nhe I site is lost in this ligation, but each cassette encodes a new C-terminal in-frame Nhe I site. Thus, additional antigen or linker cassettes can be added in an iterative fashion. Each new construct is transiently transfected into 293F cells with a matching light chain vector and at 72 hr secreted vaccine is isolated by protein A affinity and analyzed by SDS.PAGE. Constructs that express well are the preferred vectors for adding new cassettes (FIG. 1).

Figure 2:
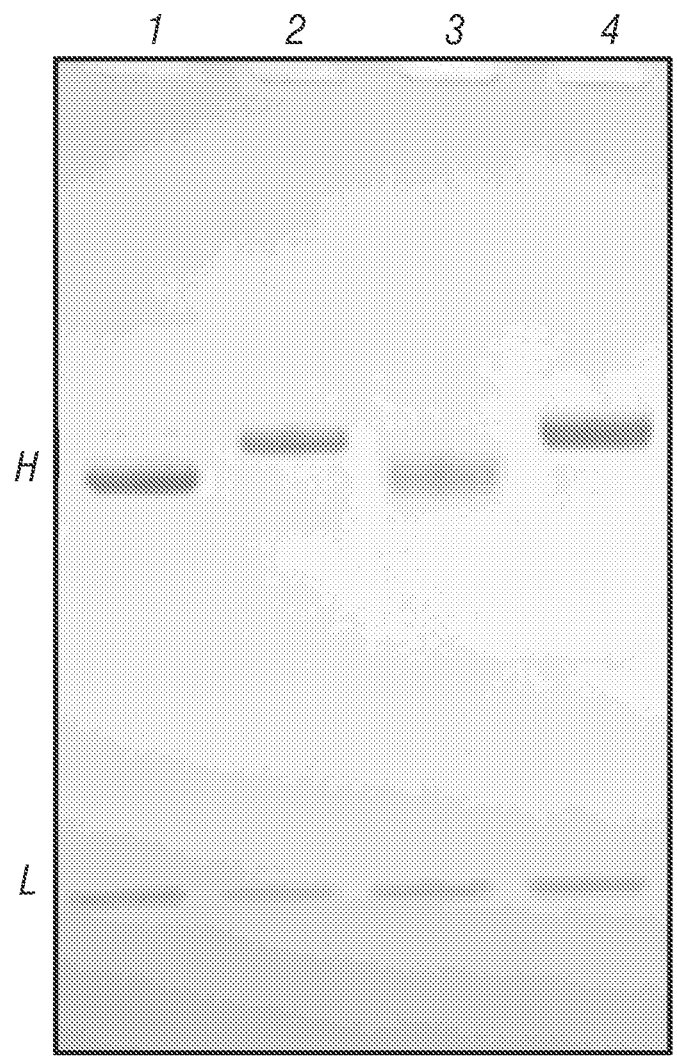
FIG. 2: SDS-PAGE analysis of protein A affinity purified anti-DC receptor antibody fused to HPV16 E6 and E7 antigens.

The inventors have engineered expression constructs with HPV16 E6 and E7 and HPV18 E6 and E7 sequences fused to antibody heavy chain C-terminii. Constructs with HPV16 or HPV18 E6 or HPV16 or HPV18 E7 sequences fused directly to an anti-dendritic cell receptor antibody heavy chain C-terminal codon failed to be secrete any detectable vaccine when co-transfected into 293F cells with a matching light chain expression vector (not shown). However, similar vectors incorporating a flexible linker sequence (Flex v1), secreted the vaccines (FIG. 2, lanes 1 and 3). Furthermore, constructs adding HPV E6 onto the Flex v1 HPV E7 vector and vice versa, also secreted vaccine (FIG. 2, lanes 2 and 4). Successful expression of such vaccines is independent on the variable region sequences. Thus, the Flex v1-HPV E6/E7 sequence was transferred to established vectors for stable expression of anti-CD40-Flex v1-HPV16 or 18 E6-HPV16E7, anti-Langerin-Flex v1-HPV16 or 18 E6-HPV16E7 and control hIgG4-Flex-v1-HPV16 or 18 E6-HPV16E7 in CHO-S cells.

Figure 3:
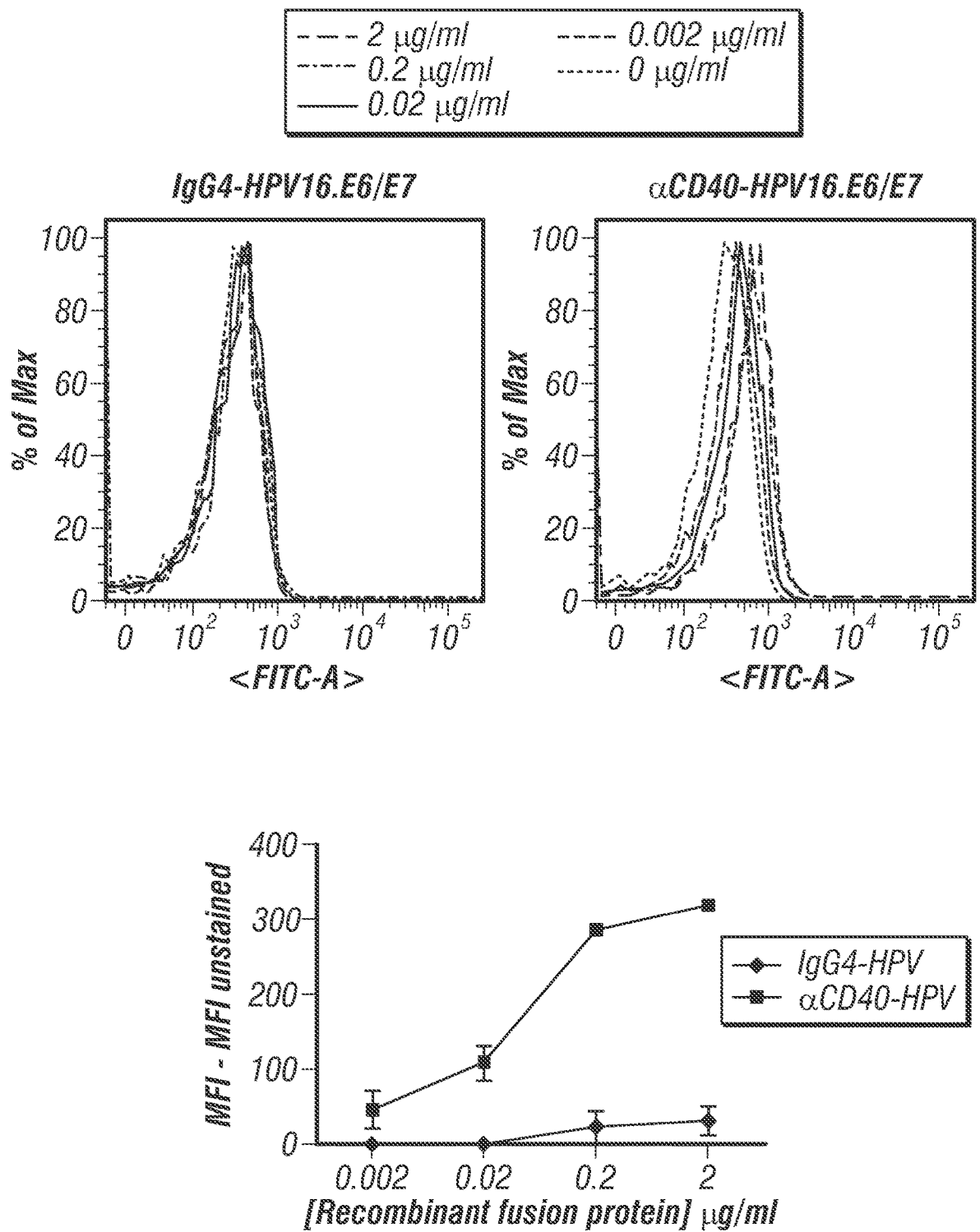
FIG. 3: Anti-CD40-HPV16.E6/7 can efficiently bind to human blood DCs.

Anti-CD40-HPV16.E6/7 can efficiently bind to DCs in peripheral blood of healthy donors. Peripheral blood mononuclear cells (PBMCs) were acquired from the blood of healthy individuals. PBMCs were incubated for 15 min on ice in the presence of different amounts of anti-CD40-HPV16.E6/7 or control IgG4-HPV16.E6/7 proteins. Cells were washed vigorously and then stained with anti-E6/7 antibodies to detect cell surface bound proteins. As shown in FIG. 3, anti-CD40-HPV16.E6/7 can efficiently bind to human blood DCs (CD3-CD19-CD14-HLA-DR+CD11c+). In contrast, IgG4-HPV16.E6/7 did not bind to the same DCs.

Anti-CD40-HPV18.E6/7 also bound to DCs in peripheral blood of healthy donors (data not shown).

Figure 4:
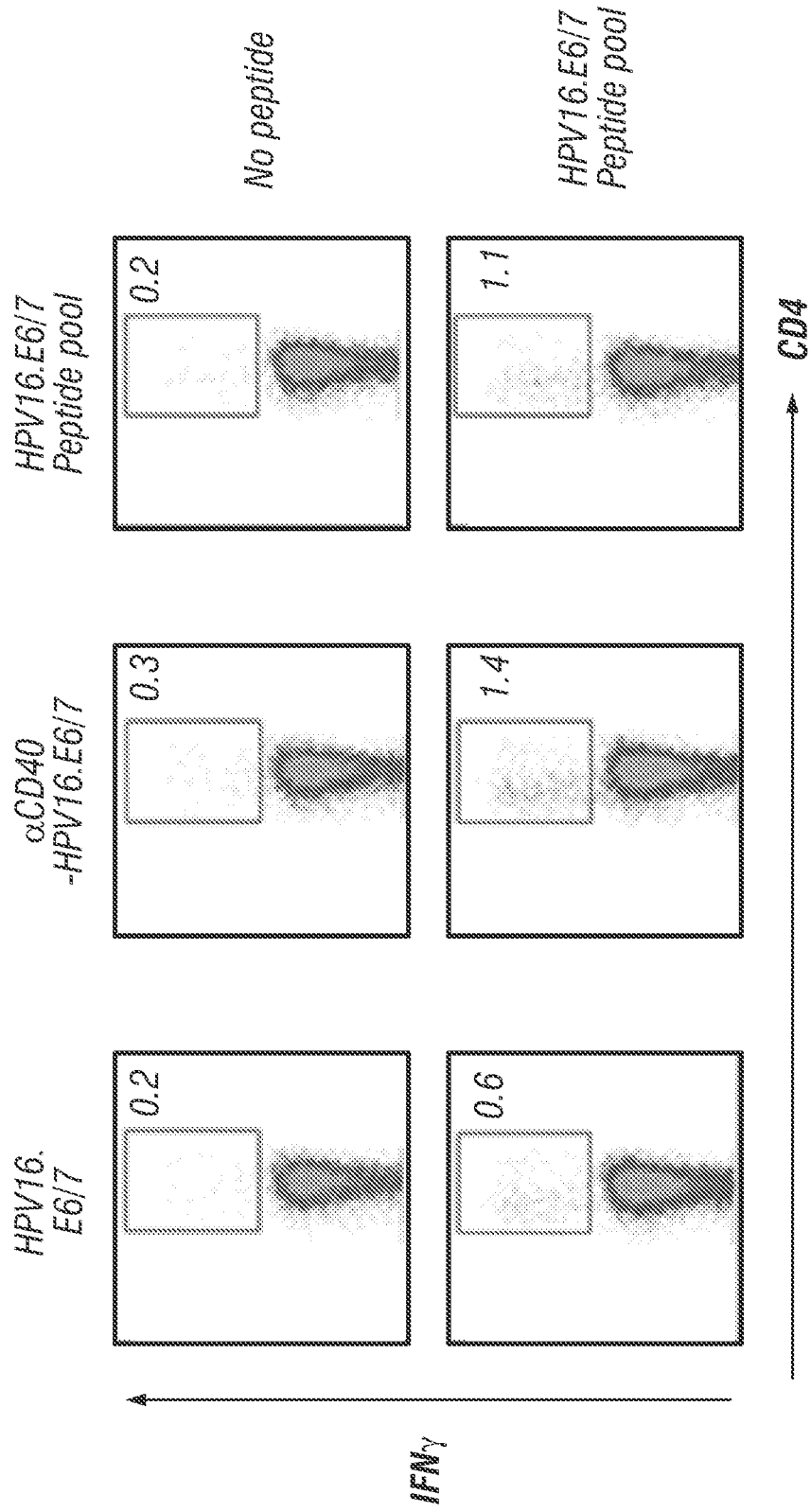
FIG. 4: Anti-CD40-HPV16.E6/7 can elicit HPV16.E6/7-specific CD4+ and CD8+ T-cell responses.
Figure 4:
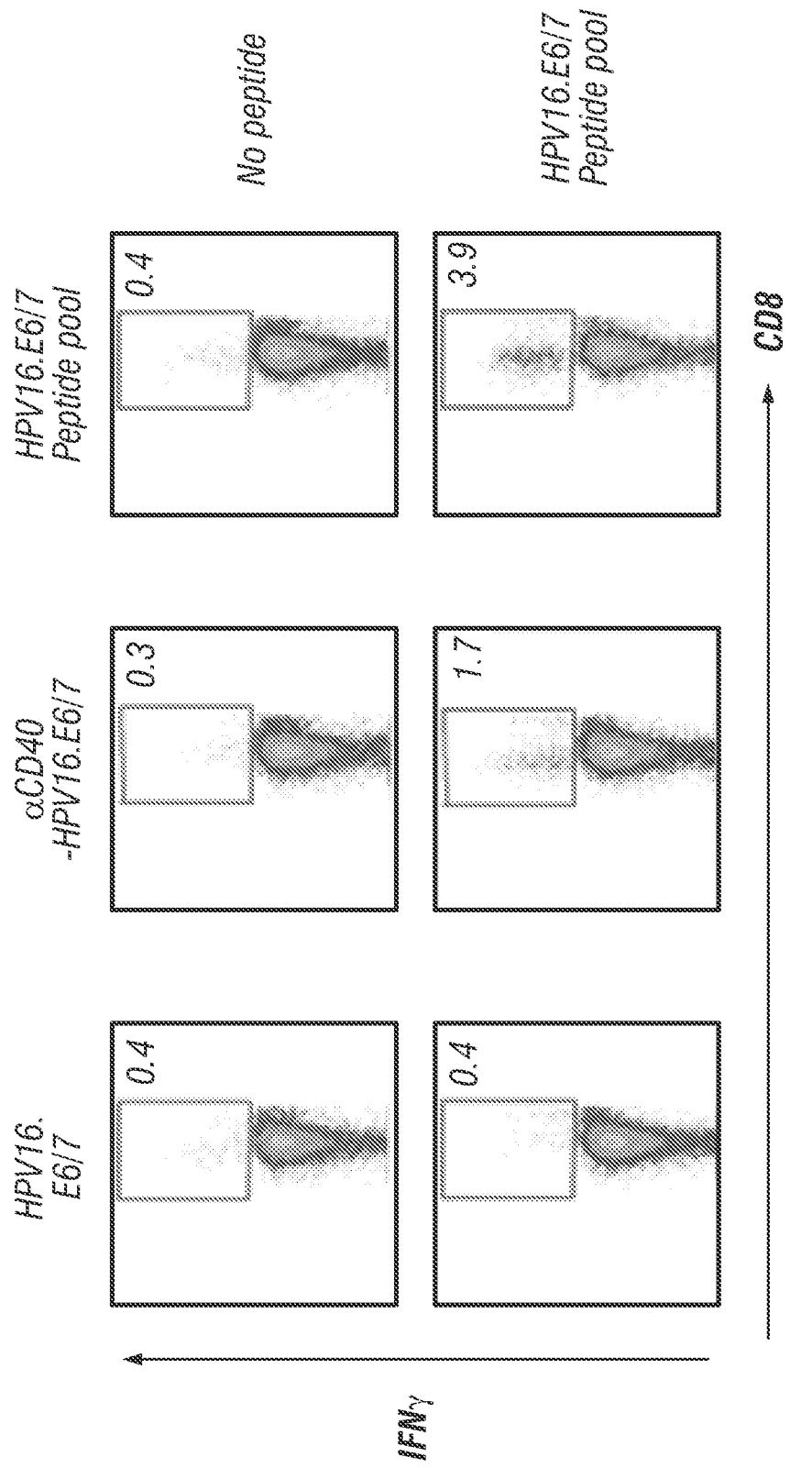

Anti-CD40-HPV16.E6/7 can efficiently activate E6/7-specific memory CD4+ and CD8+ T cells from HPV-related cancer patients. Evaluated next was the in vitro immunogenicity of anti-CD40-HPV16.E6/7 using PBMCs from HPV-positive head and neck cancer patients. Patient PBMCs were loaded with recombinant HPV16.E6/7 proteins, anti-CD40-HPV16.E6/7, or peptide pool of HPV16.E6/7 proteins. In this experiment, the same molar concentration of E6/7 in each protein was applied to compare the levels of E6/7-specific IFNg-expressing CD4+ and CD8+ T cell responses. After 7 days in vitro culture, PBMCs were restimulated for 5 h with peptide pool of E6/7 in the presence of brefeldin A and then cells were stained for IFNg expression. FIG. 4 shows that anti-CD40-HPV16.E6/7 was more efficient than HPV16.E6/7 at eliciting IFNg+CD4+ and IFNg+CD8+ T cell responses. The levels of HPV16.E6/7-specific IFNg+CD4+ T cell responses elicited with anti-CD40-HPV16.E6/7 was similar to those elicited by the peptide pool that was used as a positive control. Thus, our new vaccine models composed of anti-DCR and HPV antigens, including E6/7, is highly effective in activating antigen-specific cellular immune responses in the patients who have HPV-related cancers. Furthermore, such HPV antigen (E6 and E7)-specific CD8+ CTLs are expected to efficiently suppress tumor progression and could result in the rejection of tumors in patients.

Figure 5:
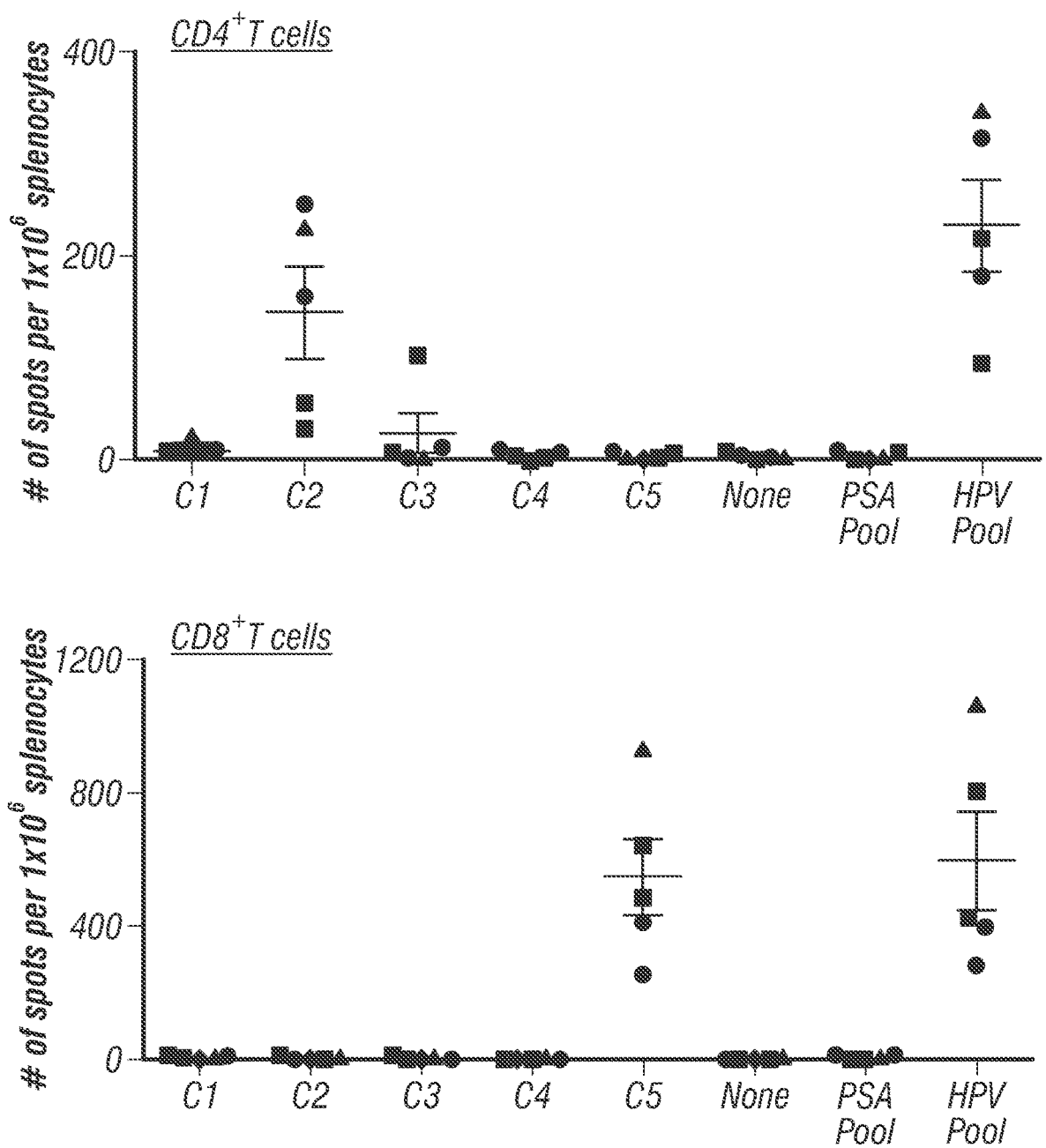
FIG. 5: Anti-CD40-HPV16.E6/7 can efficiently induce HPV16.E6/7-specific CD4+ and CD8+ T-cell responses.

Anti-CD40-HPV16.E6/7 can prime E6/7-specific CD4+ and CD8+ T cell responses in vivo. To test the in vivo immunogenicity of anti-CD40-HPV16.E6/7 vaccine, human CD40 transgenic mice were used. Five animals were immunized s.c. with 30 ug anti-CD40-HPV16.E6/7 plus poly IC on day 0 and then boosted twice with the same vaccine. On day 7 after the second boosting, CD4+ and CD8+ T cells were purified from spleens and then restimulated with one of HPV16.E6/7 peptide clusters 1-5, none, a peptide pool of prostate specific antigen (PSA), or a HPV16.E6/7 peptide pool. FIG. 5 shows that anti-CD40-HPV16.E6/7 induce HPV16 E6/7 peptide clusters 2 and 3-specific CD4+ and cluster 5-specific CD8+ T cell responses in the human CD40 transgenic mice. Importantly, the levels of E6/7-specific CD8+ T cell responses were greater than the levels of E6/7-specific CD4+ T cell responses. This indicates that anti-CD40-HPV16.E6/7 vaccines are particularly efficient in eliciting CD8+ CTLs that can kill HPV-infected cells and tumor cells. Each dot in FIG. 5 represent the data generated with a single mouse.

Figure 6:
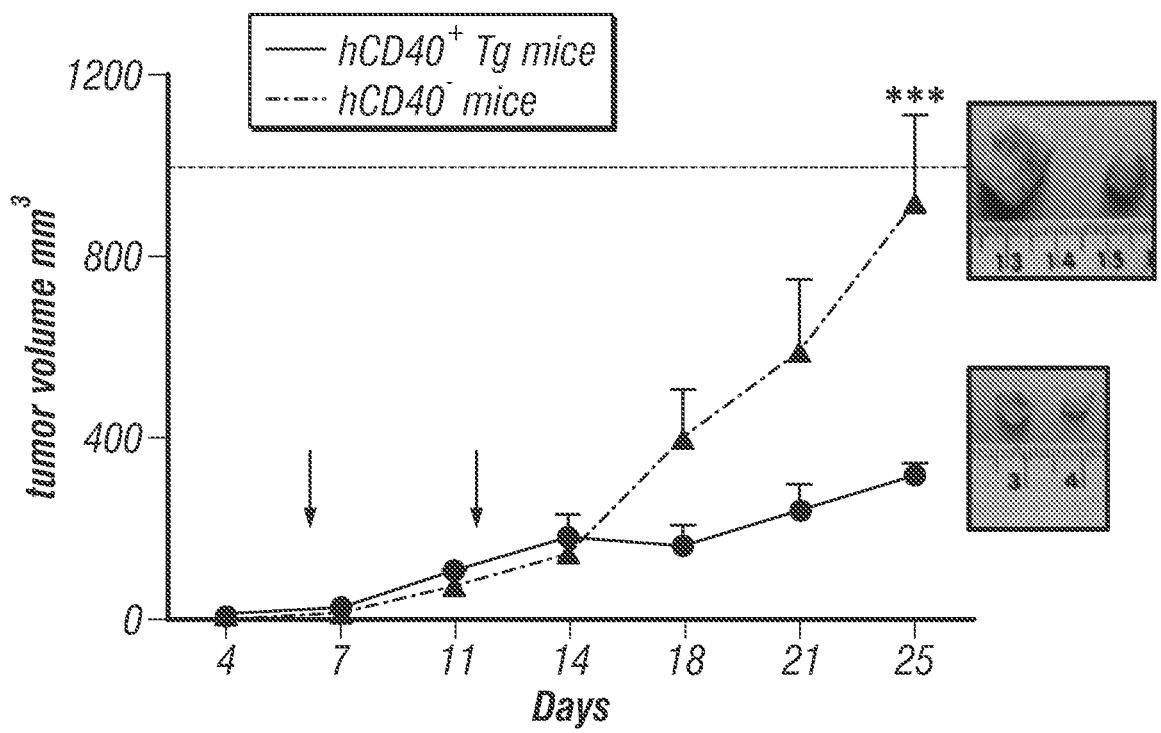
FIG. 6: Anti-CD40-HPV16.E6/7 can suppress TC-1 tumor progression in human CD40Tg mice.

Anti-CD40-HPV16.E6/7 can suppress TC-1 tumor progression in the human CD40 transgenic mice. Efficacy of anti-CD40-HPV16.E6/7 plus poly IC vaccine was tested in TC-1 challenged human CD40 transgenic mice. Two groups of animals (Human CD40+ and human CD40− mice, 5 mice per group) were challenged on day 0 with TC-1 tumor cell line subcutaneously. On days 6 and 12, animals were immunized with anti-CD40-HPV.E6/7 plus poly IC. Tumor progression was assessed and presented in FIG. 6. By day 14 after TC-1 challenge, both human CD40+ and CD40− mice developed similar sizes of tumors. In the human CD40− animals TC-1 tumor progressed quickly and reached 1000 mm 3 on day 25 after the challenge. However, TC-1 tumor progression in the human CD40+ mice was significantly delayed. Our data demonstrate that anti-CD40-HPV16.E6/7 vaccine targets human CD40 and thus elicits E6/7-specific CD8+ CTLs, as shown in FIG. 5, that suppress TC-1 tumor progression in the animals.

Figure 7:
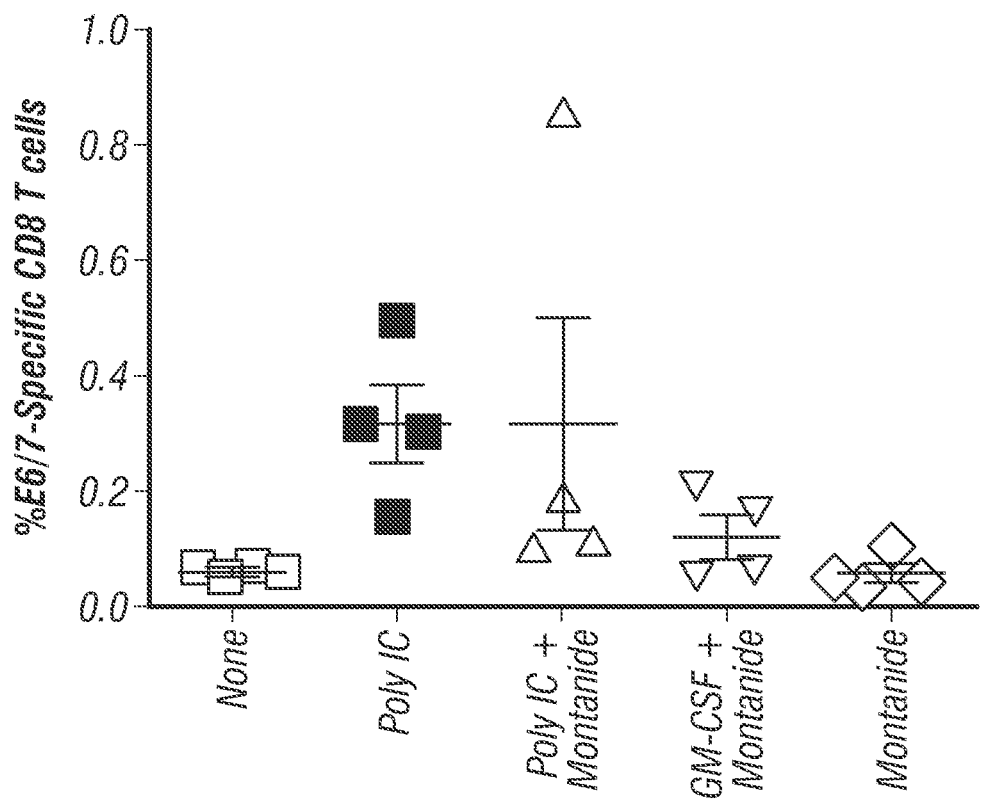
FIG. 7: Effect of adjuvant co-administration with anti-CD40-HPV16.E6/7.

The effects of poly IC, poly IC plus montanide, GM-CSF plus montanide, and montanide alone on the immunogenicity of anti-CD40-HPV.E6/7 vaccine was tested in the human CD40 transgenic mice. Four animals in each group were immunized s.c. with 30 ug anti-CD40-HPV.E6/7 alone or anti-CD40-HPV16.E6/7 with indicated adjuvants (FIG. 7). After 7 days, blood from individual animals were harvested and stained with tetramer. As shown in the figure below, poly IC was able to effectively promote anti-CD40-HPV16.E6/7-specific CD8+ T cell responses. Montanide alone or GM-CSF in montanide did not significantly promote E6/7-specific CD8+ T cell responses.

Sequences below are based on the humanized 12E12 anti-human CD40 VK2 VH2 antibody—protein sequences are the expected mature secreted protein sequence and the DNA sequences include the initiator ATG and the leader peptide region. Alternately, the HPV18 sequences can be grafted onto the C-terminus of the VK2 chain and a broader spectrum vaccine produced by combining this with the HPV16 sequences on the VH2 H chain.

| | | |
|---|---|---|
| HPV 16 E6 | see below | SEQ ID NO: 1 |
| HPV 16 E7 | see below | SEQ ID NO: 2 |
| HPV 18 E6 | see below | SEQ ID NO: 3 |
| HPV 18 E7 | see below | SEQ ID NO: 4 |
| Flexv1 | see below | SEQ ID NO: 5 |
| f1 | see below | SEQ ID NO: 6 |
| hAnti-CD40 VK2-LV-hIgGK-C | see below | SEQ ID NO: 7 |
| hAnti-CD40 VH2-LV-hIgG4H-C | see below | SEQ ID NO: 8 |
| Anti-CD40 12E12 light chain variable region | see below | SEQ ID NO: 9 |
| Anti-CD40 12E12 heavy chain variable region | see below | SEQ ID NO: 10 |
| Anti-CD40 12E12 CDR1L | SASQGI SNYLN | SEQ ID NO: 11 |
| Anti-CD40 12E12 CDR2L | YTSILHS | SEQ ID NO: 12 |
| Anti-CD40 12E12 CDR3L | QQFNKL PPT | SEQ ID NO: 13 |
| Anti-CD40 12E12 CDR1H | GFTFSD YYMY | SEQ ID NO: 14 |
| Anti-CD40 12E12 CDR2H | YINSGGGST YYPDTVKG | SEQ ID NO: 15 |
| Anti-CD40 12E12 CDR3H | RGLPFHA MDY | SEQ ID NO: 16 |

HPV 16 E6
(SEQ ID NO: 1)
MHQKRTAMFQDPQERPRKLPQLCTELQTTIHDIILECVYCKQQLLRREVGDFAFRDL

CIVYRDGNPYAVCDKCLKFYSKISEYRHYCYSVYGTTLEQQYNKPLCDLLIRCINCQ

KPLCPE

HPV 16 E7
(SEQ ID NO: 2)
MHGDTPTLHEYMLDLQPETTDLYGYGQLNDSSEEEDEIDGPAGQAEPDRAHYNIVTF

CCK

HPV 18 E6
(SEQ ID NO: 3)
MARFEDPTRRPYKLPDLCTELNTSLQDIEITCVYCKTVLELTEVGEFAFKDLFVVYRD

SIPHAACHKCIDFYSRIRELRHYSDSVYGDTLEKLINTGLYNLLIRCLRCQKPLNP

HPV 18 E7
(SEQ ID NO: 4)
MHGPKATLQDIVLHLEPQNEIPVDLLGHGQLSDSEEENDEIDGVNHQHLPARRAEPQ

RHTMLCMCCK

Flexv1
(SEQ ID NO: 5)
QTPTNTISVTPTNNSTPTNNSNPKPNP f1
(SEQ ID NO: 6)
SSVSPTTSVHPTPTSVPPTPTKSSP hAnti-CD40VK2-LV-hIgGK-C
(SEQ ID NO: 7)
DIQMTQSPSSLSASVGDRVTITCSASQGISNYLNWYQQKPGKAVKLLIYYTSILHSGV

PSRFSGSGSGTDYTLTISSLQPEDFATYYCQQFNKLPPTFGGGTKLEIKRTVAAPSVFIF

PPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC hAnti-CD40VH2-LV-hIgG4H-C
(SEQ ID NO: 8)
EVKLVESGGGLVQPGGSLKLSCATSGFTFSDYYMYWVRQAPGKGLEWVAYINSGG

GSTYYPDTVKGRFTISRDNAKNTLYLQMNSLRAEDTAVYYCARRGLPFHAMDYWG

QGTLVTVSSAKTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

Anti-CD4012E12 light chain variable region
(SEQ ID NO: 9)
DIQMTQTTSSLSASLGDRVTISCSASQGISNYLNWYQQKPDGTVKLLIYYTSILHSGVP

SRFSGSGSGTDYSLTIGNLEPEDIATYYCQQFNKLPPTFGGGTKLEIK

Anti-CD4012E12 heavy chain variable region
(SEQ ID NO: 10)
CEVKLVESGGGLVQPGGSLKLSCATSGFTFSDYYMYWVRQTPEKRLEWVAYINSGG

GSTYYPDTVKGRFTISRDNAKNTLYLQMSRLKSEDTAMYYCARRGLPFHAMDYWG

QGTSVTVS hAnti-CD40VK2-LV-hIgGK-C
(SEQ ID NO: 17)
DIQMTQSPSSLSASVGDRVTITCSASQGISNYLNWYQQKPGKAVKLLIYYTSILHSGV

PSRFSGSGSGTDYTLTISSLQPEDFATYYCQQFNKLPPTFGGGTKLEIKRTVAAPSVFIF

-continued

PPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC hAnti-CD40VK2-LV-hIgGK-C DNA sequence (includes
the leader peptide region)
(SEQ ID NO: 18)
ATGAGGGTCCCCGCTCAGCTCCTGGGGCTCCTGCTGCTCTGGCTCCCAGGCGCGC

GATGTGATATCCAGATGACACAGAGCCCTTCCTCCCTGTCTGCCTCTGTGGGAGA

CAGAGTCACCATCACCTGCAGTGCAAGTCAGGGCATTAGCAATTATTTAAACTGG

TATCAGCAGAAACCAGGCAAGGCCGTTAAACTCCTGATCTATTACACATCAATTT

TACACTCAGGAGTCCCATCAAGGTTCAGTGGCAGTGGGTCTGGGACAGATTATAC

CCTCACCATCAGCTCCCTGCAGCCTGAAGATTTCGCCACTTACTATTGTCAGCAG

TTTAATAAGCTTCCTCCGACGTTCGGTGGAGGCACCAAACTCGAGATCAAACGAA

CTGTGGCTGCACCATCTGTCTTCATCTTCCCGCCATCTGATGAGCAGTTGAAATCT

GGAACTGCCTCTGTTGTGTGCCTGCTGAATAACTTCTATCCCAGAGAGGCCAAAG

TACAGTGGAAGGTGGATAACGCCCTCCAATCGGGTAACTCCCAGGAGAGTGTCA

CAGAGCAGGACAGCAAGGACAGCACCTACAGCCTCAGCAGCACCCTGACGCTGA

GCAAAGCAGACTACGAGAAACACAAAGTCTATGCCTGCGAAGTCACCCATCAGG

GCCTGAGCTCGCCCGTCACAAAGAGCTTCAACAGGGGAGAGTGTTAG hAnti-CD40VH2-LV-hIgG4H-C-Flex-v1-HPV16-E6-HPV16-E7-f1
(Bold, italicized single underline sequence
is HPV16 E6; bold, italicized double underline
sequence is HPV16 E7; non-bolded, non-
italicized single underlined (Flexv1) and
non-bolded, non-italicized double underlined
(f1) sequences are flexible glycosylated
linker sequences)
(SEQ ID NO: 19)
EVKLVESGGGLVQPGGSLKLSCATSGFTFSDYYMYWVRQAPGKGLEWVAYINSGG

GSTYYPDTVKGRFTISRDNAKNTLYLQMNSLRAEDTAVYYCARRGLPFHAMDYWG

QGTLVTVSSAKTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGKAS<u>QTPTN</u>

<u>TISVTPTNNSTPTNNSNPKPNPAS</u>*MHQKRTAMFQDPQERPRKLPQLCTELQTTIHDII*

*LECVYCKQQLLRREVGDFAFRDLCIVYRDGNPYAVCDKCLKFYSKISEYRHYCYSVY*

*GTTLEQQYNKPLCDLLIRCINCQKPLCPEA*S<u>MHGDTPTLHEYMLDLQPETTDLYGYG</u>

<u>QLNDSSEEEDEIDGPAGQAEPDRAHYNIVTFCCK</u>AS<u>SSVSPTTSVHPTPTSVPPTPTKSSP</u>

AS hAnti-CD40VH2-LV-hIgG4H-C-Flex-v1-HPV16-E6-
HPV16-E7-f1 DNA sequence
(includes the leader peptide region)
(SEQ ID NO: 20)
ATGGGTTGGAGCCTCATCTTGCTCTTCCTTGTCGCTGTTGCTACGCGTGTCCACTC

CGAAGTGAAGCTGGTGGAGTCTGGGGGAGGCTTAGTGCAGCCCGGAGGGTCCCT

GAAACTCTCCTGTGCAACCTCTGGATTCACTTTCAGTGACTATTACATGTATTGGG

TTCGCCAGGCCCCAGGCAAGGGCCTGGAGTGGGTCGCATACATTAATTCTGGTGG

-continued
```
TGGTAGCACCTATTATCCAGACACTGTAAAGGGCCGATTCACCATCTCCAGAGAC

AATGCCAAGAACACCCTGTACCTGCAAATGAACAGCCTGAGGGCCGAGGACACA

GCCGTGTATTACTGTGCAAGACGGGGGTTACCGTTCCATGCTATGGACTATTGGG

GTCAAGGAACCCTGGTCACCGTCTCCTCAGCCAAAACGAAGGGCCCATCCGTCTT

CCCCCTGGCGCCCTGCTCCAGGAGCACCTCCGAGAGCACAGCCGCCCTGGGCTGC

CTGGTCAAGGACTACTTCCCCGAACCGGTGACGGTGTCGTGGAACTCAGGCGCCC

TGACCAGCGGCGTGCACACCTTCCCGGCTGTCCTACAGTCCTCAGGACTCTACTC

CCTCAGCAGCGTGGTGACCGTGCCCTCCAGCAGCTTGGGCACGAAGACCTACAC

CTGCAACGTAGATCACAAGCCCAGCAACACCAAGGTGGACAAGAGAGTTGAGTC

CAAATATGGTCCCCCATGCCCACCCTGCCCAGCACCTGAGTTCGAAGGGGGACC

ATCAGTCTTCCTGTTCCCCCCAAAACCCAAGGACACTCTCATGATCTCCCGGACC

CCTGAGGTCACGTGCGTGGTGGTGGACGTGAGCCAGGAAGACCCCGAGGTCCAG

TTCAACTGGTACGTGGATGGCGTGGAGGTGCATAATGCCAAGACAAAGCCGCGG

GAGGAGCAGTTCAACAGCACGTACCGTGTGGTCAGCGTCCTCACCGTCCTGCACC

AGGACTGGCTGAACGGCAAGGAGTACAAGTGCAAGGTCTCCAACAAAGGCCTCC

CGTCCTCCATCGAGAAAACCATCTCCAAAGCCAAAGGGCAGCCCCGAGAGCCAC

AGGTGTACACCCTGCCCCCATCCCAGGAGGAGATGACCAAGAACCAGGTCAGCC

TGACCTGCCTGGTCAAAGGCTTCTACCCCAGCGACATCGCCGTGGAGTGGGAGA

GCAATGGGCAGCCGGAGAACAACTACAAGACCACGCCTCCCGTGCTGGACTCCG

ACGGCTCCTTCTTCCTCTACAGCAGGCTAACCGTGGACAAGAGCAGGTGGCAGG

AGGGGAATGTCTTCTCATGCTCCGTGATGCATGAGGCTCTGCACAACCACTACAC

ACAGAAGAGCCTCTCCCTGTCTCTGGGTAAAGCTAGTCAGACCCCCACCAACACC

ATCAGCGTGACCCCCACCAACAACAGCACCCCCACCAACAACAGCAACCCCAAG

CCCAACCCCGCTAGTATGCACCAAAAAAGGACCGCAATGTTTCAGGACCCCCAA

GAGAGGCCCCGCAAACTGCCACAACTTTGCACGGAGCTGCAGACAACAATACAT

GACATCATTCTCGAATGTGTTTACTGTAAGCAGCAGTTGTTGCGAAGAGAAGTGG

GAGACTTCGCTTTCAGAGACCTGTGTATCGTATATCGCGATGGCAATCCTTATGC

CGTCTGCGATAAATGCCTCAAGTTTTACTCCAAGATCAGCGAGTACCGGCACTAC

TGTTACTCTGTGTATGGGACTACCCTCGAACAGCAGTATAACAAGCCGCTGTGCG

ATCTCCTTATCCGGTGCATTAACTGCCAGAAGCCACTGTGTCCTGAGGCTAGTAT

GCACGGGGATACCCCCACACTCCACGAATACATGCTTGATTTGCAACCTGAAACG

ACCGACCTGTACGGCTATGGTCAGCTGAATGACTCCAGCGAGGAAGAGGATGAG

ATTGACGGACCGGCAGGCCAGGCCGAGCCAGACCGGGCTCATTATAACATCGTG

ACTTTCTGCTGTAAGGCTAGTAGCAGCGTGAGCCCCACCACCAGCGTGCACCCCA

CCCCCACCAGCGTGCCCCCACCCCCACCAAGAGCAGCCCCGCTAGCTGA
```

-continued hAnti-CD40VH2-LV-hIgG4H-C-Flex-v1-HPV18E6-HPV18E7-f1
(Bold, italicized single underline sequence
is HPV18 E6; bold, italicized double underline
sequence is HPV18 E7; non-bolded, non-
italicized single underlined (Flexv1) and
non-bolded, non-italicized double underlined
(f1) sequences are flexible glycosylated linker
sequences)

(SEQ ID NO: 21)

EVKLVESGGGLVQPGGSLKLSCATSGFTFSDYYMYWVRQAPGKGLEWVAYINSGG

GSTYYPDTVKGRFTISRDNAKNTLYLQMNSLRAEDTAVYYCARRGLPFHAMDYWG

QGTLVTVSSAKTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRVESKYGPPC

PPCPAPEFEGGPSVFLFPPKPKDTLMISRTPEVTCVVVDVSQEDPEVQFNWYVDGVE

VHNAKTKPREEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGKAS<u>QTPTN</u>

<u>TISVTPTNNSTPTNNSNPKPNPAS</u>*MARFEDPTRRPYKLPDLCTELNTSLQDIEITCVYC*

*KTVLELTEVGEFAFKDLFVVYRDSIPHAACHKCIDFYSRIRELRHYSDSVYGDTLEKL*

*TNTGLYNLLIRCLRCQKPLNPAS*MHGPKATLQDIVLHLEPQNEIPVDLLGHGQLSDS

EEENDEIDGVNHQHLPARRAEPQRHTMLCMCCKAS<u>SSVSPTTSVHPTPTSVPPTPTKSSP</u>

<u>AS</u> hAnti-CD40VH2-LV-hIgG4H-C-Flex-v1-HPV18E6-HPV18E7-f1
DNA sequence
(includes the leader peptide region)

(SEQ ID NO: 22)

ATGGGTTGGAGCCTCATCTTGCTCTTCCTTGTCGCTGTTGCTACGCGTGTCCACTC

CGAAGTGAAGCTGGTGGAGTCTGGGGGAGGCTTAGTGCAGCCCGGAGGGTCCCT

GAAACTCTCCTGTGCAACCTCTGGATTCACTTTCAGTGACTATTACATGTATTGGG

TTCGCCAGGCCCCAGGCAAGGGCCTGGAGTGGGTCGCATACATTAATTCTGGTGG

TGGTAGCACCTATTATCCAGACACTGTAAAGGGCCGATTCACCATCTCCAGAGAC

AATGCCAAGAACACCCTGTACCTGCAAATGAACAGCCTGAGGGCCGAGGACACA

GCCGTGTATTACTGTGCAAGACGGGGGTTACCGTTCCATGCTATGGACTATTGGG

GTCAAGGAACCCTGGTCACCGTCTCCTCAGCCAAAACGAAGGGCCCATCCGTCTT

CCCCCTGGCGCCCTGCTCCAGGAGCACCTCCGAGAGCACAGCCGCCCTGGGCTGC

CTGGTCAAGGACTACTTCCCCGAACCGGTGACGGTGTCGTGGAACTCAGGCGCCC

TGACCAGCGGCGTGCACACCTTCCCGGCTGTCCTACAGTCCTCAGGACTCTACTC

CCTCAGCAGCGTGGTGACCGTGCCCTCCAGCAGCTTGGGCACGAAGACCTACAC

CTGCAACGTAGATCACAAGCCCAGCAACACCAAGGTGGACAAGAGAGTTGAGTC

CAAATATGGTCCCCCATGCCCACCCTGCCCAGCACCTGAGTTCGAAGGGGGACC

ATCAGTCTTCCTGTTCCCCCCAAAACCCAAGGACACTCTCATGATCTCCCGGACC

CCTGAGGTCACGTGCGTGGTGGTGGACGTGAGCCAGGAAGACCCCGAGGTCCAG

TTCAACTGGTACGTGGATGGCGTGGAGGTGCATAATGCCAAGACAAAGCCGCGG

GAGGAGCAGTTCAACAGCACGTACCGTGTGGTCAGCGTCCTCACCGTCCTGCACC

AGGACTGGCTGAACGGCAAGGAGTACAAGTGCAAGGTCTCCAACAAAGGCCTCC

CGTCCTCCATCGAGAAAACCATCTCCAAAGCCAAAGGGCAGCCCCGAGAGCCAC

AGGTGTACACCCTGCCCCCATCCCAGGAGGAGATGACCAAGAACCAGGTCAGCC

```
-continued
TGACCTGCCTGGTCAAAGGCTTCTACCCCAGCGACATCGCCGTGGAGTGGGAGA

GCAATGGGCAGCCGGAGAACAACTACAAGACCACGCCTCCCGTGCTGGACTCCG

ACGGCTCCTTCTTCCTCTACAGCAGGCTAACCGTGGACAAGAGCAGGTGGCAGG

AGGGGAATGTCTTCTCATGCTCCGTGATGCATGAGGCTCTGCACAACCACTACAC

ACAGAAGAGCCTCTCCCTGTCTCTGGGTAAAGCTAGTCAGACCCCCACCAACACC

ATCAGCGTGACCCCCACCAACAACAGCACCCCCACCAACAACAGCAACCCCAAG

CCCAACCCCGCTAGTATGGCCAGATTCGAGGATCCAACACGCCGACCTTACAAAT

TGCCGGACCTTTGCACGGAGCTGAACACTTCCCTGCAGGACATAGAAATTACCTG

CGTCTACTGCAAGACCGTTCTCGAACTGACAGAAGTAGGCGAGTTTGCGTTTAAA

GATCTGTTCGTGGTGTATCGGGATAGCATTCCCCACGCAGCTTGTCATAAGTGTA

TCGACTTCTATTCTAGGATCCGGGAGCTCAGACACTATAGCGATTCCGTGTACGG

CGACACACTTGAGAAGCTCACTAACACCGGGCTGTACAACCTCCTGATCCGGTGC

TTGAGGTGTCAGAAACCCCTGAATCCTGCTAGTATGCACGGGCCTAAGGCCACAC

TGCAAGATATTGTCCTCCATCTCGAACCCCAGAATGAGATACCAGTGGACCTTCT

GGGCCACGGACAGTTGTCCGATAGCGAGGAGGAAAACGACGAAATCGACGGTGT

TAACCACCAGCACTTGCCGGCTCGGAGGGCAGAGCCCCAGAGACATACCATGCT

GTGCATGTGTTGCAAAGCTAGTAGCAGCGTGAGCCCCACCACCAGCGTGCACCC

CACCCCCACCAGCGTGCCCCCACCCCCACCAAGAGCAGCCCCGCTAGCTGA
```

Example 2— Recombinant Fusion Proteins of Anti-DC Receptors (DCRs), TLR Ligands, and HPV Sequences Below is an example of a TLR2 ligand (tri-acylated cohesin, expressed in *E. coli*) where the C residue in the D1 leader domain is lipidated, this can be non-covalently attached to anti-CD40-HPV vaccine when the anti-CD40 has, e.g., a Dockerin domain fused to either the C-terminus or the L chain or the H chain C-terminus distal to the HPV E6/7 sequences.

```
D1-6His-Cohesin-Nhe-Spe-Not
(note that additional
cancer antigen sequences can be added
distal to the Cohesin domain)
                                    (SEQ ID NO: 23)
MKKLLIAAMMAAALAACSQEAKQEVKEAVQAVESDVKDTA

MGSSHHHHHHSSGLVPRGSHMASMDLDAVRIKVDTVNAKP

GDTVNIPVRESGIPSKGIANCDFVYSYDPNVLEIIEIKPG

ELIVDPNPTKSFDTAVYPDRKMIVFLFAEDSGTGAYAITK

DGVFATIVAKVKEGAPNGLSVIKFVEVGGFANNDLVEQKT

QFFDGGVNVGDTTEPATPTTPVTTPTTTDDLDAASLIKTS

EF

D1-6His-Cohesin-Nhe-Spe-Not DNA sequence
                                    (SEQ ID NO: 24)
ATGAAAAAACTGCTGATTGCCGCCATGATGGCTGCAGCTC

TGGCCGCATGCAGCCAGGAAGCCAAACAGGAAGTGAAAGA

AGCCGTGCAGGCCGTGGAAAGCGATGTGAAAGATACCGCC

ATGGGCAGCAGCCATCATCATCATCATCACAGCAGCGGCC

TGGTGCCGCGCGGCAGCCATATGGCTAGTATGGATCTGGA

TGCAGTAAGGATTAAAGTGGACACAGTAAATGCAAAACCG

GGAGACACAGTAAATATACCTGTAAGATTCAGTGGTATAC

CATCCAAGGGAATAGCAAACTGTGACTTTGTATACAGCTA

TGACCCGAATGTACTTGAGATAATAGAGATAAAACCGGGA

GAATTGATAGTTGACCCGAATCCTACCAAGAGCTTTGATA

CTGCAGTATATCCTGACAGAAAGATGATAGTATTCCTGTT

TGCGGAAGACAGCGGAACAGGAGCGTATGCAATAACTAAA

GACGGAGTATTTGCTACGATAGTAGCGAAAGTAAAAGAAG

GAGCACCTAACGGGCTCAGTGTAATCAAATTTGTAGAAGT

AGGCGGATTTGCGAACAATGACCTTGTAGAACAGAAGACA

CAGTTCTTTGACGGTGGAGTAAATGTTGGAGATACAACAG

AACCTGCAACACCTACAACACCTGTAACAACACCGACAAC

AACAGATGATCTAGATGCAGCTAGCTTAATTAAAACTAGT

GAATTCTGA
```

Below is an example of an anti-CD40 L chain bearing a preferred TLR5L Flagellin domain (shown underlined). This would be co-transfected with the matching H chain bearing HPV E6/7 antigen at the C-terminus.

(SEQ ID NO: 26)
hAnti-CD40VK2-LV-hIgGK-C-Flgn1-Flgn2
(underlined sequence is Flagellin domain)
DIQMTQSPSSLSASVGDRVTITCSASQGISNYLNWYQQKP

GKAVKLLIYYTSILHSGVPSRFSGSGSGTDYTLTISSLQP

EDFATYYCQQFNKLPPTFGGGTKLEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGECAS<u>IERLSSGLRINSAKDDAAGQAIAN</u>

<u>RFTANIKGLTQASRNANDGISIAQTTEGALNEINNNLQRV</u>

<u>RELAVQSANSTNSQSDLDSIQAEITQRLNEIDRVSGQTQF</u>

<u>NGVKVLAQDNTLTIQVGANDGETIDIDLKQINSQTLGLDS</u>

<u>LNVQASQPELAEAAAKTTENPLQKIDAALAQVDALRSDLG</u>

<u>AVQNRFNSAITNLGNTVNNLSEARSRIEDSDYATEVSNMS</u>

<u>RAQILQAS</u> hAnti-CD40VK2-LV-hIgGK-C-Flgn1-Flgn2
DNA sequence
(SEQ ID NO: 25)
ATGAGGGTCCCCGCTCAGCTCCTGGGGCTCCTGCTGCTCT

GGCTCCCAGGCGCGCGATGTGATATCCAGATGACACAGAG

CCCTTCCTCCCTGTCTGCCTCTGTGGGAGACAGAGTCACC

ATCACCTGCAGTGCAAGTCAGGGCATTAGCAATTATTTAA

ACTGGTATCAGCAGAAACCAGGCAAGGCCGTTAAACTCCT

GATCTATTACACATCAATTTTACACTCAGGAGTCCCATCA

AGGTTCAGTGGCAGTGGGTCTGGGACAGATTATACCCTCA

CCATCAGCTCCCTGCAGCCTGAAGATTTCGCCACTTACTA

TTGTCAGCAGTTTAATAAGCTTCCTCCGACGTTCGGTGGA

GGCACCAAACTCGAGATCAAACGAACTGTGGCTGCACCAT

CTGTCTTCATCTTCCCGCCATCTGATGAGCAGTTGAAATC

TGGAACTGCCTCTGTTGTGTGCCTGCTGAATAACTTCTAT

CCCAGAGAGGCCAAAGTACAGTGGAAGGTGGATAACGCCC

TCCAATCGGGTAACTCCCAGGAGAGTGTCACAGAGCAGGA

CAGCAAGGACAGCACCTACAGCCTCAGCAGCACCCTGACG

CTGAGCAAAGCAGACTACGAGAAACACAAAGTCTATGCCT

GCGAAGTCACCCATCAGGGCCTGAGCTCGCCCGTCACAAA

GAGCTTCAACAGGGGAGAGTGTGCTAGTATCGAGCGTCTG

TCTTCTGGTCTGCGTATCAACAGCGCGAAAGACGATGCGG

CAGGTCAGGCGATTGCTAACCGTTTTACCGCGAACATCAA

AGGTCTGACTCAGGCTTCCCGTAACGCTAACGACGGTATC

TCCATCGCGCAGACCACTGAAGGCGCGCTGAACGAAATCA

ACAACAACCTGCAGCGTGTGCGTGAACTGGCGGTTCAGTC

TGCTAACAGCACTAACTCCCAGTCTGACCTCGACTCCATC

CAGGCTGAAATCACCCAGCGCCTGAACGAAATCGACCGTG

TATCCGGTCAGACTCAGTTCAACGGCGTGAAAGTCCTGGC

GCAGGACAACACCCTGACCATCCAGGTTGGTGCCAACGAC

GGTGAAACTATCGATATCGATCTGAAGCAGATCAACTCTC

AGACCCTGGGCCTGGATTCACTGAACGTGCAGGCTAGTCA

ACCAGAGCTGGCGGAAGCAGCCGCTAAAACCACCGAAAAC

CCGCTGCAGAAAATTGATGCCGCGCTGGCGCAGGTGGATG

CGCTGCGCTCTGATCTGGGTGCGGTACAAAACCGTTTCAA

CTCCGCTATCACCAACTTGGGCAATACCGTAAACAACCTG

TCTGAAGCGCGTAGCCGTATCGAAGATTCCGACTACGCGA

CCGAAGTTTCCAACATGTCTCGCGCGCAGATTCTGCAGGC

TAGCTGA

Below is an example of analogous HPV 18 E6/7 sequences fused to DC-targeting antibody H chain (in this case anti-Langerin). This can be fused instead to the H chain of the preferred antiCD40 antibody in place of the HPV 16 sequences, or fused downstream of the HPV 16 sequences, or fused to the anti-CD40 L chain—in each case making a vaccine bearing both HPV 16 and HPV 18 sequences.

Anti-Langerin15B10H-LV-hIgG4H-C-
HPV18E7-HPV18E6-f1
(Bold, italicized single underline
sequence is HPV18 E6; bold,
italicized double underline
sequence is HPV18 E7; non-
bolded, non-italicized double
underlined (f1) sequence is
a flexible glycosylated linker
sequence)
(SEQ ID NO: 27)
QVQLRQSGPELVKPGASVKMSCKASGYTFTDYVISWV

KQRTGQGLEWIGDIYPGSGYSFYNENFKGKATLTADK

SSTTAYMQLSSLTSEDSAVYFCATYYNYPFAYWGQGT

LVTVSAAKTTGPSVFPLAPCSRSTSESTAALGCLVKD

YFPEPVTVSWNSGALTSGVHTFPAVLQSSGLYSLSSV

VTVPSSSLGTKTYTCNVDHKPSNTKVDKRVESKYGPP

CPPCPAPEFEGGPSVFLFPPKPKDTLMISRTPEVTCV

VVDVSQEDPEVQFNWYVDGVEVHNAKTKPREEQFNST

YRVVSVLTVLHQDWLNGKEYKCKVSNKGLPSSIEKTI

SKAKGQPREPQVYTLPPSQEEMTKNQVSLTCLVKGFY

PSDIAVEWESNGQPENNYKTTPPVLDSDGSFFLYSRL

TVDKSRWQEGNVFSCSVMHEALHNHYTQKSLSLSLGK

A*MHGPKATLQDIVLHLEPQNEIPVDLLGHGQ*

*LSDSEEENDEIDGVNHQHLPARRAEPQRHTMLCMC*CK

AS*MARFEDPTRRPYKLPDLCTELNTSLQDIEITCV*

*YCKTVLELTEVGEFAFKDLFVVYRDSIPHAACHKCID*

*FYSRIRELRHYSDSVYGDTLEKLTNTGLYNLLIRCLR*

*CQKPLNP*A<u>SSVSPTTSVHPTPTSVPPTPTKSSP</u>AS

Anti-Langerin15B10H-LV-hIgG4H-C-HPV18E7-HPV18E6-f1 DNA sequence
(SEQ ID NO: 28)

ATGGAATGGAGGATCTTTCTCTTCATCCTGTCAGGAA

CTGCAGGTGTCCACTCCCAGGTTCAGCTGCGGCAGTC

TGGACCTGAGCTGGTGAAGCCTGGGGCTTCAGTGAAG

ATGTCCTGCAAGGCTTCTGGATACACATTTACTGACT

ATGTTATAAGTTGGGTGAAGCAGAGAACTGGACAGGG

CCTTGAGTGGATTGGAGATATTTATCCTGGAAGTGGT

TATTCTTTCTACAATGAGAACTTCAAGGGCAAGGCCA

CACTGACTGCAGACAAATCCTCCACCACAGCCTACAT

GCAGCTCAGCAGCCTGACATCTGAGGACTCTGCGGTC

TATTTCTGTGCAACCTACTATAACTACCCTTTTGCTT

ACTGGGGCCAAGGGACTCTGGTCACTGTCTCTGCAGC

CAAAACAACGGGCCCATCCGTCTTCCCCCTGGCGCCC

TGCTCCAGGAGCACCTCCGAGAGCACAGCCGCCCTGG

GCTGCCTGGTCAAGGACTACTTCCCCGAACCGGTGAC

GGTGTCGTGGAACTCAGGCGCCCTGACCAGCGGCGTG

CACACCTTCCCGGCTGTCCTACAGTCCTCAGGACTCT

ACTCCCTCAGCAGCGTGGTGACCGTGCCCTCCAGCAG

CTTGGGCACGAAGACCTACACCTGCAACGTAGATCAC

AAGCCCAGCAACACCAAGGTGGACAAGAGAGTTGAGT

CCAAATATGGTCCCCCATGCCCACCCTGCCCAGCACC

TGAGTTCGAAGGGGGACCATCAGTCTTCCTGTTCCCC

CCAAAACCCAAGGACACTCTCATGATCTCCCGGACCC

CTGAGGTCACGTGCGTGGTGGTGGACGTGAGCCAGGA

AGACCCCGAGGTCCAGTTCAACTGGTACGTGGATGGC

GTGGAGGTGCATAATGCCAAGACAAAGCCGCGGGAGG

AGCAGTTCAACAGCACGTACCGTGTGGTCAGCGTCCT

CACCGTCCTGCACCAGGACTGGCTGAACGGCAAGGAG

TACAAGTGCAAGGTCTCCAACAAAGGCCTCCCGTCCT

CCATCGAGAAAACCATCTCCAAAGCCAAAGGGCAGCC

CCGAGAGCCACAGGTGTACACCCTGCCCCCATCCCAG

GAGGAGATGACCAAGAACCAGGTCAGCCTGACCTGCC

TGGTCAAAGGCTTCTACCCCAGCGACATCGCCGTGGA

GTGGGAGAGCAATGGGCAGCCGGAGAACAACTACAAG

ACCACGCCTCCCGTGCTGGACTCCGACGGCTCCTTCT

TCCTCTACAGCAGGCTAACCGTGGACAAGAGCAGGTG

GCAGGAGGGGAATGTCTTCTCATGCTCCGTGATGCAT

GAGGCTCTGCACAACCACTACACACAGAAGAGCCTCT

CCCTGTCTCTGGGTAAAGCTAGTATGCACGGGCCTAA

GGCCACACTGCAAGATATTGTCCTCCATCTCGAACCC

CAGAATGAGATACCAGTGGACCTTCTGGGCCACGGAC

AGTTGTCCGATAGCGAGGAGGAAAACGACGAAATCGA

CGGTGTTAACCACCAGCACTTGCCGGCTCGGAGGGCA

GAGCCCCAGAGACATACCATGCTGTGCATGTGTTGCA

AAGCTAGTATGGCCAGATTCGAGGATCCAACACGCCG

ACCTTACAAATTGCCGGACCTTTGCACGGAGCTGAAC

ACTTCCCTGCAGGACATAGAAATTACCTGCGTCTACT

GCAAGACCGTTCTCGAACTGACAGAAGTAGGCGAGTT

TGCGTTTAAAGATCTGTTCGTGGTGTATCGGGATAGC

ATTCCCCACGCAGCTTGTCATAAGTGTATCGACTTCT

ATTCTAGGATCCGGGAGCTCAGACACTATAGCGATTC

CGTGTACGGCGACACACTTGAGAAGCTCACTAACACC

GGGCTGTACAACCTCCTGATCCGGTGCTTGAGGTGTC

AGAAACCCCTGAATCCTGCTAGTAGCAGCGTGAGCCC

CACCACCAGCGTGCACCCCACCCCCACCAGCGTGCCC

CCCACCCCCACCAAGAGCAGCCCCGCTAGCTGA

Example 3—CD40 Targeting HPV Vaccine (CD40HVac)

Figures 8A, 8B:
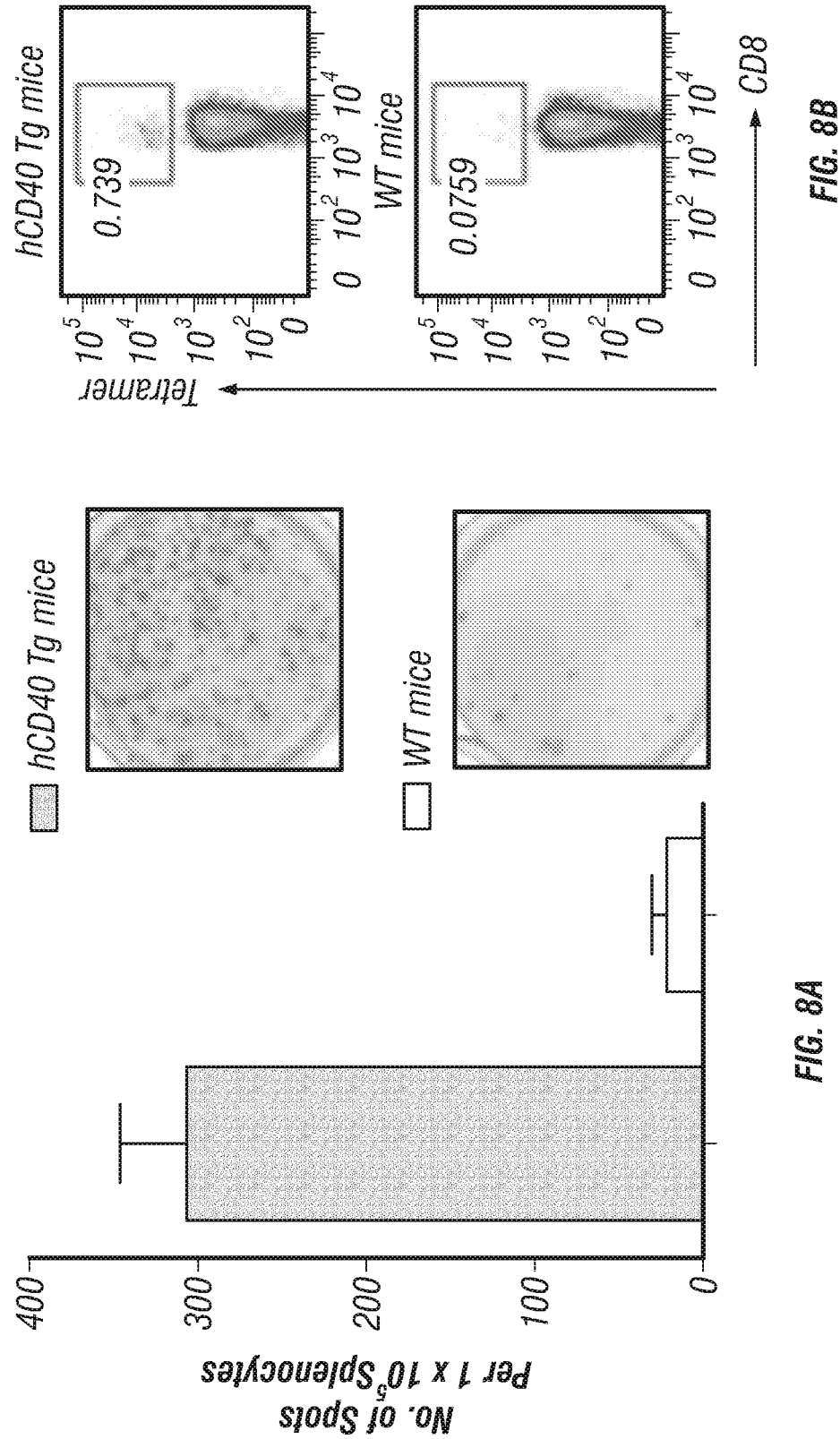
FIGS. 8A-8B: CD40HVac plus poly IC induces E6/7-specific CD8+ T cells in hCD40 transgenic animals.

CD40HVac plus poly IC induces E6/7-specific CD8+ CTLs in human CD40 transgenic B6 (hCD40Tg) mice. hCD40Tg and WT animals (5 mice/group) were immunized subcutaneously (SC) with 30 μg CD40HVac plus 50 μg poly IC in PBS (100 μl) and boosted twice two weeks apart. The amounts of CD40HVac and poly IC were predetermined in separate experiments. Seven days after the second boosting, IFNγ ELISPOT was performed using purified CD8+ T cells from spleens (FIG. 8a). Compared to WT mice, hCD40Tg mice elicited increased numbers of CD8+IFNγ+ T cells. The inventors also observed that hCD40Tg mice had increased E7-specific CD8+ T cells in the blood, as measured by tetramer staining (FIG. 8b). In addition, CD40HVac plus poly IC induced greater levels of E6/7-specific CD4+ T cell responses in hCD40Tg mice than in WT animals (not shown). Taken together, the inventors concluded that CD40HVac targets human CD40 in vivo and can thus elicit E6/7-specific cellular responses. The inventors also found that CD40HVac plus poly IC (adjuvant) was more potent than CD40HVac alone at eliciting E6/7-specific T cell responses in hCD40Tg mice (data not shown), although humanized anti-CD40 antibody used in CD40HVac has an agonistic property.

Figure 9A:
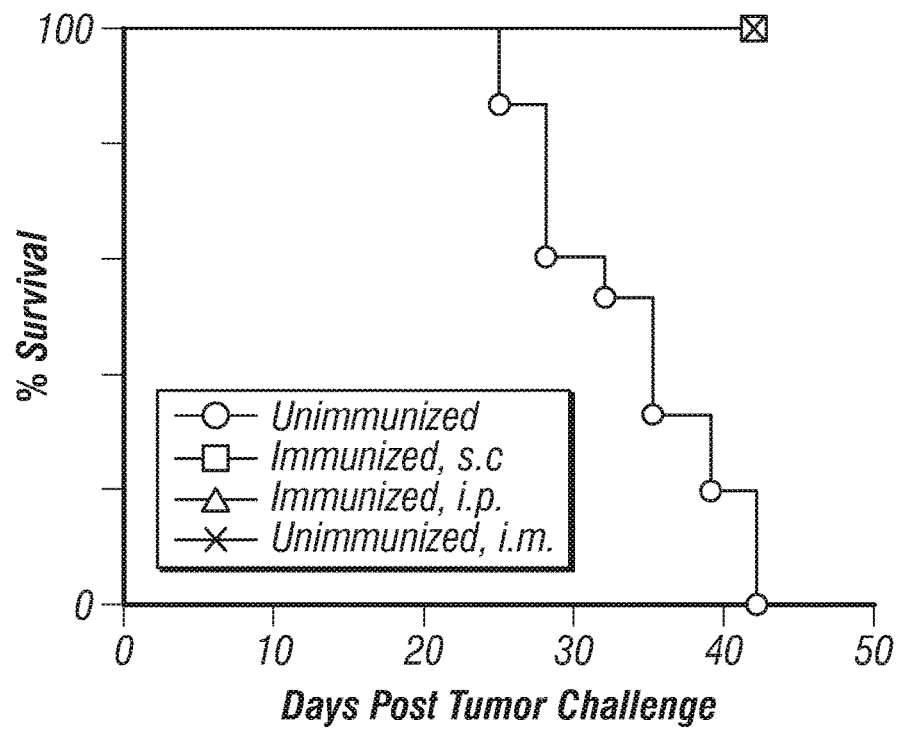
FIGS. 9A-9B: CD40HVac plus poly IC induces therapeutic immunity in hCD40Tg mice.
Figure 9B:
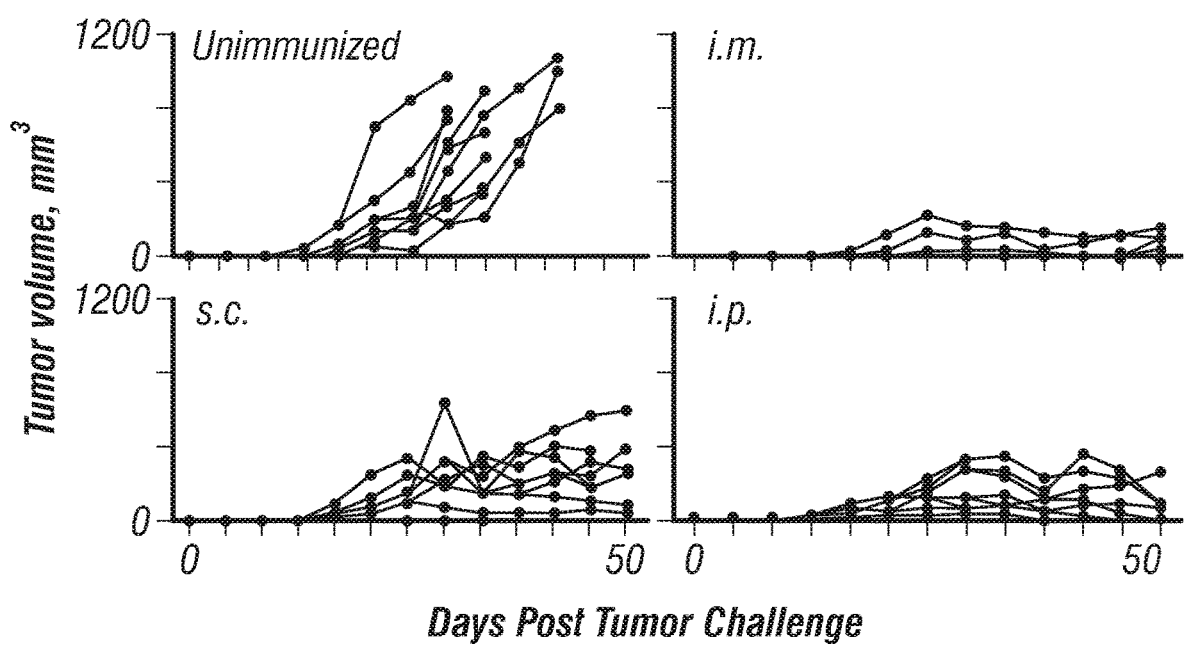

CD40HVac plus poly IC can mount therapeutic immunity in hCD40Tg animals. hCD40Tg mice (10 mice per group) were SC challenged with HPV E6/7-expressing TC-1 tumor cells (5×10⁴). The inventors confirmed that animals harbor palpable tumors on day 6 after TC-1 challenge. Animals were then immunized SC, intramuscularly (IM), or intraperitoneally (IP) with 30 μg CD40HVac plus 50 μg poly IC on days 6, 12, and 24. A control group was kept without immunization. FIG. 9a shows that all animals receiving CD40HVac plus poly IC survived while all control animals died. Injection of poly IC alone did not promote survival (data not shown). In a separate experiment, we measured progression of TC-1 tumors by assessing tumor volume (FIG. 9b). All control animals (10 mice) developed tumors and died within 40 days of TC-1 challenge. In contrast, CD40HVac plus poly IC treatment suppressed tumor progression. It is also of note that some of the treated animals developed large tumors (200-600 mm 3), and these tumors regressed over time during vaccination. Taken together, the inventors concluded that CD40HVac elicits therapeutic immunity in hCD40Tg mice. Furthermore, the data indicated that the route of immunization is an important factor that could impact the overall therapeutic efficacy of the CD40HVac regimen.

Figure 10:
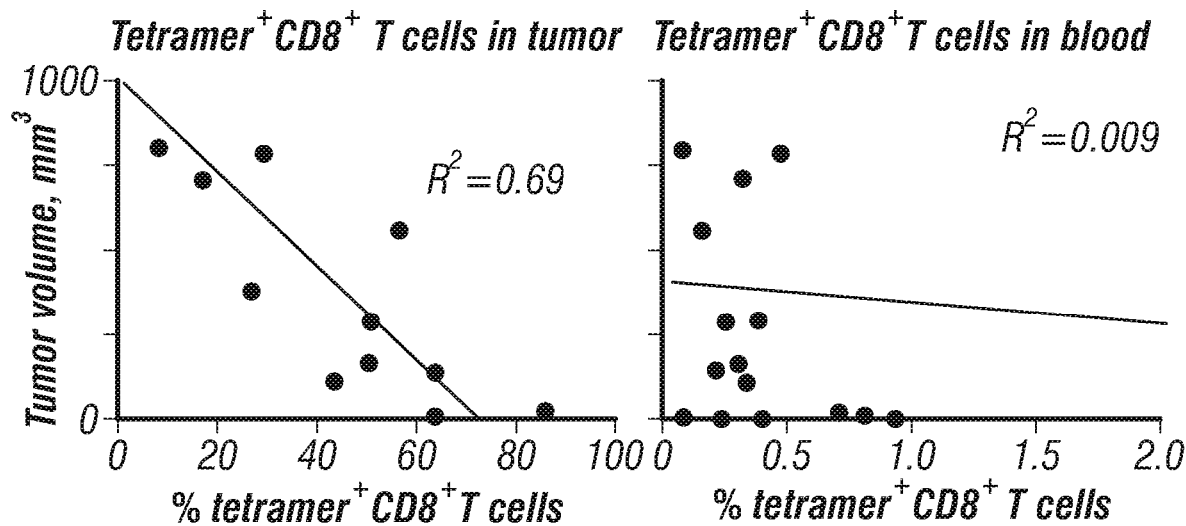
FIG. 10: The percentage of E7-specific tetramer+CD8+ T cells in tumors, but not blood, inversely correlates with tumor volume.

CD8+ CTL infiltration into tumors is critical for tumor regression. Human CD40 transgenic (hCD40Tg) mice were SC challenged with high numbers of TC-1 tumor cells ($2 \times 10^5$ cells). Animals were then immunized with 30 μg CD40HVac plus 50 μg poly IC on days 6 and 12. Without vaccination, all animals died within 25 days after the tumor challenge. On day 60, the percentages of H2-db (RAHYNIVTF) tetramer+CD8+ T cells in tumors and blood were assessed (FIG. 10). The percentage of tetramer+CD8+ T cells in the tumor (left) inversely correlates with tumor volume. There was no such correlation between the percentage of tetramer+CD8+ T cells in the blood (right) or spleen (not shown) and the tumor volume. Thus, infiltration of antigen-specific CD8+ CTLs into tumors is critical for tumor regression. Thus, we anticipate the improvement of CD40HVac efficacy by promoting effector cell infiltration into and retention within mucosal tumors.

Figure 11A:
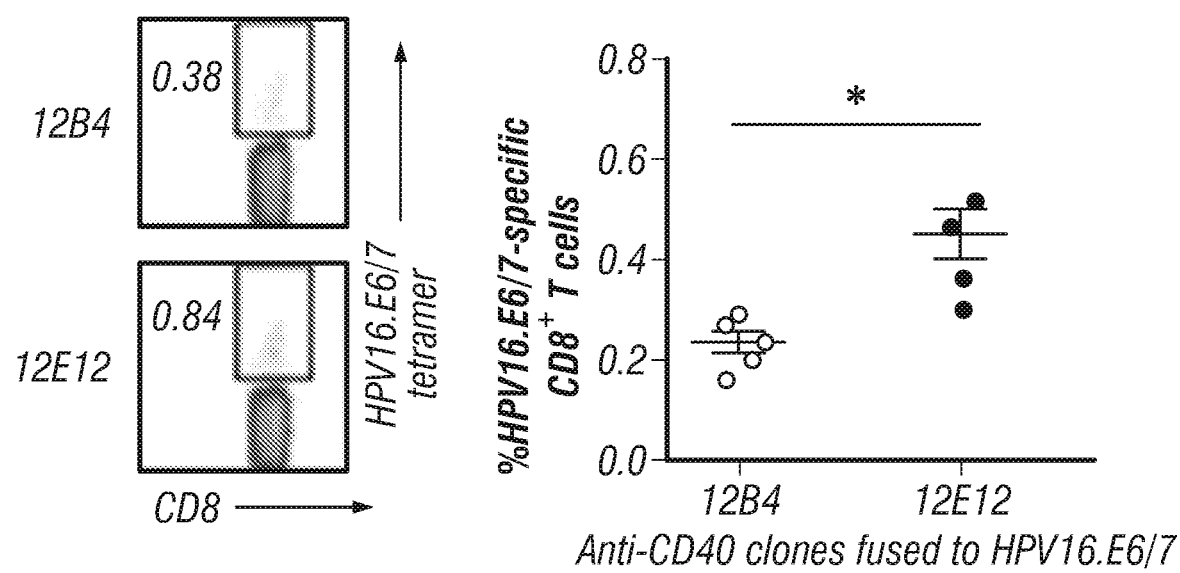
FIGS. 11A-11B: CD40HVac made with anti-CD40 (clone 12E12) is more efficient than that made with anti-CD40 (clone 12B6) at inducing E6/7-specific CD8+ T cell responses.
Figure 11B:
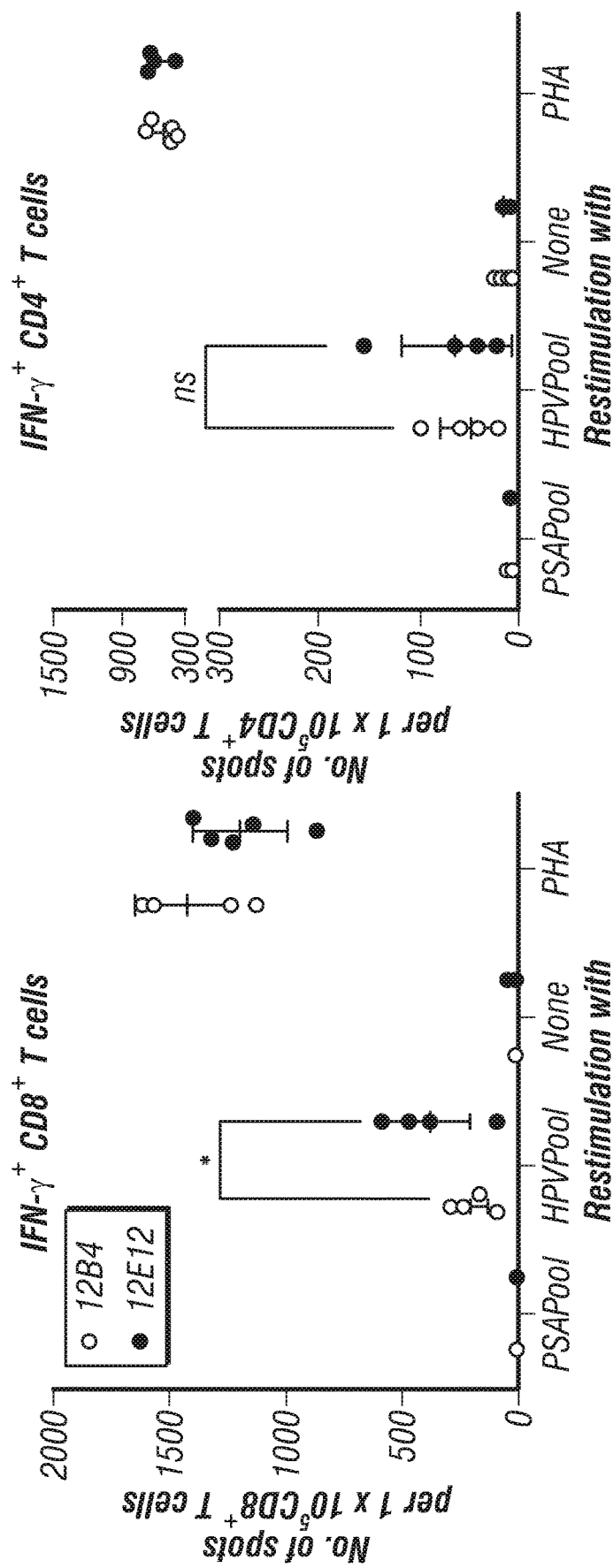

CD40HVac made with anti-CD40 (12E12 clone) is more efficient than CD40HVac made with anti-CD40 (12B4 clone) at eliciting HPV16.E6/7-specific CD8+ T cell responses. The inventors compared recombinant fusion proteins made with three different clones of anti-CD40 mAbs (12E12 and 12B4) for their ability to prime HPV16.E6/7-specific CD8+ T cell responses. The inventors used poly IC as an adjuvant. hCD40Tg animals received three doses of recombinant fusion proteins (30 μg/dose) plus poly IC (50 μg/dose) via s.c. Seven days after the third immunization, the percentage of E7-specific CD8+ T cells in the blood were determined by tetramer staining. As shown in left panel of FIG. 11a, recombinant fusion proteins made with 12E12 was more efficient than those made with 12B4 clone at inducing E6/7-specific CD8+ T cell responses. The inventors also found that anti-CD40 (12E12)-HPV16.E6/7 was more efficient than anti-CD40 (12B6)-HPV16.E6/7 at eliciting IFNγ+ CD8+ T cell responses by ELISPOT assay using splenocytes (left panel in FIG. 11b). HPV16.E6/7 fused with the two clones of anti-CD40 mAbs resulted in similar levels of E6/7-specific IFNγ+CD4+ T cell responses (right panel in FIG. 11b).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

*Antibodies: A Laboratory Manual*, Cold Spring Harbor Laboratory, 1988
Atherton et al., 1985
Ausubel et al., 1996
Barany and Merrifield, 1979
Bird et al., 1988
Burke et al., 1994
Cumber et al., 1992
Dholakia et al., 1989
*Epitope Mapping Protocols* (1996)
Glennie et al., 1987
Goding, 1986, pp. 60 61
Holliger et al, 1993
Holliger & Winter, 1999
Holt et al., 2003
Hu et al. 1996
Huston et al., 1988
Khatoon et al., 1989
King et al., 1989
Kohl et al., 2003
Kyte and Doolittle, 1982
Liu et al., 2003
McCafferty et al., 1990
Merchand et al., 1998
Merrifield, 1986
O'Shannessy et al., 1987
Owens & Haley, 1987
Pack, et al., 1992
Potter & Haley, 1983
Reiter et al., 1996
Repp et al., 1995
Ridgeway et al., 1996
Sambrook et al., 2001
Skerra, 2000
Skerra, 2001
Staerz & Bevan, 1986
Stewart and Young, 1984
Tam et al., 1983
Tigges et al., 1996
Ward, 1989
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,277,437
U.S. Pat. No. 4,275,149
U.S. Pat. No. 4,366,241
U.S. Pat. No. 4,472,509
U.S. Pat. No. 4,554,101
U.S. Pat. No. 4,879,236
U.S. Pat. No. 4,938,948
U.S. Pat. No. 5,196,066
U.S. Pat. No. 5,741,957
U.S. Pat. No. 5,750,172
U.S. Pat. No. 5,756,687

U.S. Pat. No. 5,827,690
U.S. Pat. No. 5,871,986
U.S. Pat. No. 6,091,001
U.S. Pat. No. 6,651,655
U.S. Patent Publication No. 2005/0106660
U.S. Patent Publication No. 2006/0058510
U.S. Patent Publication No. 2006/0088908
U.S. Patent Publication No. 2010/0285564
U.S. Patent Publication No. 2012/0039,916
U.S. Patent Publication No. 2012/023,102
U.S. Provisional Patent No. 61/332,465
U.S. patent application Ser. No. 12/024,036
U.S. patent application Ser. No. 12/024,897
U.S. patent application Ser. No. 12/025,010
U.S. patent application Ser. No. 12/026,095
U.S. patent application Ser. No. 12/036,138
U.S. patent application Ser. No. 12/036,158
U.S. patent application Ser. No. 12/504,463
U.S. patent application Ser. No. 12/717,778
U.S. patent application Ser. No. 12/717,789
U.S. patent application Ser. No. 12/717,804
U.S. patent Application Ser. No. 12/718,365
U.S. patent application Ser. No. 12/882,052
U.S. patent application Ser. No. 12/882,052
U.S. patent application Ser. No. 13/100,684
U.S. patent application Ser. No. 13/208,993
U.S. patent application Ser. No. 13/269,951
U.S. patent application Ser. No. 13/282,112
U.S. patent application Ser. No. 13/415,564
U.S. patent application Ser. No. 13/424,582
U.S. patent application Ser. No. 13/430,206
U.S. patent application Ser. No. 13/594,397
U.S. patent application Ser. No. 13/596,526
U.S. patent application Ser. No. 13/465,371
U.S. patent application Ser. No. 13/397,932
PCT Publication No. WO2006/056464
PCT Publication No. WO94/13804
PCT Publication No. WO 2008/103947
PCT Publication No. WO 2008/103953
PCT Publication No. WO 2008/118587
PCT Publication No. WO 2010/104747
PCT Publication No. WO 2010/104749
PCT Publication No. WO 2010/104761
PCT Publication No. WO 2012/021834
PCT Patent Application No. PCT/US92/09965
PCT Patent Application No. PCT/US13/72217
PCT Patent Application No. PCT/US2013/05839

What is claimed is:

1. One or more nucleic acids encoding a fusion protein comprising an anti-CD40antibody or fragment thereof, comprising at least three complementarity determining regions (CDRs) from each of a heavy and light chain of an anti-CD40 antibody, at least one peptide linker and at least one human papillomavirus (HPV) E6 antigen and at least one HPV E7 antigen, wherein the E6 and E7 antigens comprise an antigen with at least 90% sequence identity to SEQ ID NO: 1 and an antigen with at least 90% sequence identity to SEQ ID NO:2; and
   wherein the fusion protein comprises an amino acid sequence that has at least 95% sequence identity to SEQ ID NO: 19.

2. The one or more nucleic acids of claim 1, wherein the anti-CD40 antibody or fragment thereof is humanized.

3. The one or more nucleic acids of claim 1, wherein the fusion protein comprises peptide linkers comprising the amino acid sequences of SEQ ID NO:5 and SEQ ID NO:6.

4. The one or more nucleic acids of claim 1, wherein the three CDRs from the heavy chain of the anti-CD40 antibody comprises the amino acid sequences of SEQ ID NOs: 14-16, and wherein the three CDRs from the light chain of the anti-CD40 antibody comprises the amino acid sequences of SEQ ID NOs: 11-13.

5. One or more nucleic acids encoding a fusion protein comprising an anti-CD40antibody or fragment thereof, comprising at least three complementarity determining regions (CDRs) from each of a heavy and light chain of an anti-CD40 antibody, at least one peptide linker and at least one human papillomavirus (HPV) E6 antigen and at least one HPV E7 antigen, wherein the E6 and E7 antigens comprise an antigen with at least 90% sequence identity to SEQ ID NO: 3 and an antigen with at least 90% sequence identity to SEQ ID NO:4; and wherein the fusion protein comprises an amino acid sequence that has at least 95% sequence identity to SEQ ID NO:21.

6. The one or more nucleic acids of claim 5, wherein the anti-CD40 antibody or fragment thereof is humanized.

7. The one or more nucleic acids of claim 5, wherein the three CDRs from the heavy chain of the anti-CD40 antibody comprises the amino acid sequences of SEQ ID NOs: 14-16, and wherein the three CDRs from the light chain of the anti-CD40 antibody comprises the amino acid sequences of SEQ ID NOs: 11-13.

8. The one or more nucleic acids of claim 5, wherein the fusion protein comprises peptide linkers comprising the amino acid sequences of SEQ ID NO:5 and SEQ ID NO:6.

9. The one or more nucleic acids of claim 5, wherein the three CDRs from the heavy chain of the anti-CD40 antibody comprises the amino acid sequences of SEQ ID NOs: 14-16, and wherein the three CDRs from the light chain of the anti-CD40 antibody comprises the amino acid sequences of SEQ ID NOs: 11-13.

10. A vector comprising the one or more nucleic acids of claim 1.

11. A vector comprising the one or more nucleic acids of claim 5.

12. An isolated host cell comprising the one or more nucleic acids of claim 1.

13. An isolated host cell comprising the one or more nucleic acids of claim 5.

14. A method of making a fusion protein comprising expressing the one or more nucleic acids of claim 1 in a host cell and isolating the fusion protein.

15. A method of making a fusion protein comprising expressing the one or more nucleic acids of claim 5 in a host cell and isolating the fusion protein.

16. A method of making a fusion protein comprising incubating an host cell comprising the one or more nucleic acids of claim 1 and isolating the fusion protein.

17. A method of making a fusion protein comprising incubating an host cell comprising the one or more nucleic acids of claim 5 and isolating the fusion protein.

* * * * *

SEQUENCE LISTING

```
Sequence total quantity: 31
SEQ ID NO: 1            moltype = AA  length = 120
FEATURE                 Location/Qualifiers
source                  1..120
                        mol_type = protein
                        organism = synthetic construct
SEQUENCE: 1
MHQKRTAMFQ DPQERPRKLP QLCTELQTTI HDIILECVYC KQQLLRREVG DFAFRDLCIV   60
YRDGNPYAVC DKCLKFYSKI SEYRHYCYSV YGTTLEQQYN KPLCDLLIRC INCQKPLCPE  120

SEQ ID NO: 2            moltype = AA  length = 60
FEATURE                 Location/Qualifiers
source                  1..60
                        mol_type = protein
                        organism = synthetic construct
SEQUENCE: 2
MHGDTPTLHE YMLDLQPETT DLYGYGQLND SSEEEDEIDG PAGQAEPDRA HYNIVTFCCK   60

SEQ ID NO: 3            moltype = AA  length = 114
FEATURE                 Location/Qualifiers
source                  1..114
                        mol_type = protein
                        organism = synthetic construct
SEQUENCE: 3
MARFEDPTRR PYKLPDLCTE LNTSLQDIEI TCVYCKTVLE LTEVGEFAFK DLFVVYRDSI   60
PHAACHKCID FYSRIRELRH YSDSVYGDTL EKLTNTGLYN LLIRCLRCQK PLNP        114

SEQ ID NO: 4            moltype = AA  length = 67
FEATURE                 Location/Qualifiers
source                  1..67
                        mol_type = protein
                        organism = synthetic construct
SEQUENCE: 4
MHGPKATLQD IVLHLEPQNE IPVDLLGHGQ LSDSEEENDE IDGVNHQHLP ARRAEPQRHT   60
MLCMCCK                                                             67

SEQ ID NO: 5            moltype = AA  length = 27
FEATURE                 Location/Qualifiers
source                  1..27
                        mol_type = protein
                        organism = synthetic construct
SEQUENCE: 5
QTPTNTISVT PTNNSTPTNN SNPKPNP                                       27

SEQ ID NO: 6            moltype = AA  length = 25
FEATURE                 Location/Qualifiers
source                  1..25
```

```
                         mol_type = protein
                         organism = synthetic construct
SEQUENCE: 6
SSVSPTTSVH PTPTSVPPTP TKSSP                                          25

SEQ ID NO: 7             moltype = AA   length = 214
FEATURE                  Location/Qualifiers
source                   1..214
                         mol_type = protein
                         organism = synthetic construct
SEQUENCE: 7
DIQMTQSPSS LSASVGDRVT ITCSASQGIS NYLNWYQQKP GKAVKLLIYY TSILHSGVPS    60
RFSGSGSGTD YTLTISSLQP EDFATYYCQQ FNKLPPTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 8             moltype = AA   length = 446
FEATURE                  Location/Qualifiers
source                   1..446
                         mol_type = protein
                         organism = synthetic construct
SEQUENCE: 8
EVKLVESGGG LVQPGGSLKL SCATSGFTFS DYYMYWVRQA PGKGLEWVAY INSGGGSTYY    60
PDTVKGRFTI SRDNAKNTLY LQMNSLRAED TAVYYCARRG LPFHAMDYWG QGTLVTVSSA   120
KTKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVMHEA LHNHYTQKSL SLSLGK                                       446

SEQ ID NO: 9             moltype = AA   length = 107
FEATURE                  Location/Qualifiers
source                   1..107
                         mol_type = protein
                         organism = synthetic construct
SEQUENCE: 9
DIQMTQTTSS LSASLGDRVT ISCSASQGIS NYLNWYQQKP DGTVKLLIYY TSILHSGVPS    60
RFSGSGSGTD YSLTIGNLEP EDIATYYCQQ FNKLPPTFGG GTKLEIK                107

SEQ ID NO: 10            moltype = AA   length = 119
FEATURE                  Location/Qualifiers
source                   1..119
                         mol_type = protein
                         organism = synthetic construct
SEQUENCE: 10
CEVKLVESGG GLVQPGGSLK LSCATSGFTF SDYYMYWVRQ TPEKRLEWVA YINSGGGSTY    60
YPDTVKGRFT ISRDNAKNTL YLQMSRLKSE DTAMYYCARR GLPFHAMDYW GQGTSVTVS   119

SEQ ID NO: 11            moltype = AA   length = 11
FEATURE                  Location/Qualifiers
source                   1..11
                         mol_type = protein
                         organism = synthetic construct
SEQUENCE: 11
SASQGISNYL N                                                         11

SEQ ID NO: 12            moltype = AA   length = 7
FEATURE                  Location/Qualifiers
source                   1..7
                         mol_type = protein
                         organism = synthetic construct
SEQUENCE: 12
YTSILHS                                                               7

SEQ ID NO: 13            moltype = AA   length = 9
FEATURE                  Location/Qualifiers
source                   1..9
                         mol_type = protein
                         organism = synthetic construct
SEQUENCE: 13
QQFNKLPPT                                                             9

SEQ ID NO: 14            moltype = AA   length = 10
FEATURE                  Location/Qualifiers
source                   1..10
                         mol_type = protein
                         organism = synthetic construct
SEQUENCE: 14
```

```
GFTFSDYYMY                                                               10

SEQ ID NO: 15           moltype = AA  length = 17
FEATURE                 Location/Qualifiers
source                  1..17
                        mol_type = protein
                        organism = synthetic construct
SEQUENCE: 15
YINSGGGSTY YPDTVKG                                                       17

SEQ ID NO: 16           moltype = AA  length = 10
FEATURE                 Location/Qualifiers
source                  1..10
                        mol_type = protein
                        organism = synthetic construct
SEQUENCE: 16
RGLPFHAMDY                                                               10

SEQ ID NO: 17           moltype = AA  length = 214
FEATURE                 Location/Qualifiers
source                  1..214
                        mol_type = protein
                        organism = synthetic construct
SEQUENCE: 17
DIQMTQSPSS LSASVGDRVT ITCSASQGIS NYLNWYQQKP GKAVKLLIYY TSILHSGVPS         60
RFSGSGSGTD YTLTISSLQP EDFATYYCQQ FNKLPPTFGG GTKLEIKRTV AAPSVFIFPP        120
SDEQLKSGTA SVVCLLNNFY PREAKVQWKV DNALQSGNSQ ESVTEQDSKD STYSLSSTLT        180
LSKADYEKHK VYACEVTHQG LSSPVTKSFN RGEC                                    214

SEQ ID NO: 18           moltype = DNA  length = 705
FEATURE                 Location/Qualifiers
source                  1..705
                        mol_type = other DNA
                        organism = synthetic construct
SEQUENCE: 18
atgagggtcc ccgctcagct cctgggctc ctgctgctct ggctcccagg cgcgcgatgt          60
gatatccaga tgacacagag cccttcctcc tgtctgcct ctgtgggaga cagagtcacc        120
atcacctgca gtgcaagtca gggcattagc aattatttaa actggtatca gcagaaacca       180
ggcaaggccg ttaaactcct gatctattac acatcaattt tacactcagg agtcccatca       240
aggttcagtg gcagtgggtc tgggacagat tataccctca ccatcagctc cctgcagcct       300
gaagatttcg ccacttacta ttgtcagcag tttaataagc ttcctccgac gttcggtgga       360
ggcaccaaac tcgagatcaa acgaactgtg gctgcaccat ctgtcttcat cttcccgcca       420
tctgatgagc agttgaaatc tggaactgcc tctgttgtgt gcctgctgta taacttcgat       480
cccagagagg ccaaagtaca gtggaaggtg gataacgccc tccaatcggg taactcccag       540
gagagtgtca cagagcagga cagcaaggac agcacctaca gcctcagcag caccctgacg       600
ctgagcaaag cagactacga gaaacacaaa gtctatgcct gcgaagtcac ccatcagggc       660
ctgagctcgc ccgtcacaaa gagcttcaac aggggagagt gttag                       705

SEQ ID NO: 19           moltype = AA  length = 688
FEATURE                 Location/Qualifiers
source                  1..688
                        mol_type = protein
                        organism = synthetic construct
SEQUENCE: 19
EVKLVESGGG LVQPGGSLKL SCATSGFTFS DYYMYWVRQA PGKGLEWVAY INSGGGSTYY         60
PDTVKGRFTI SRDNAKNTLY LQMNSLRAED TAVYYCARRG LPFHAMDYWG QGTLVTVSSA        120
KTKGPSVFPL APCSRSTSES TAALGCLVKD YFPEPVTVSW NSGALTSGVH TFPAVLQSSG        180
LYSLSSVVTV PSSSLGTKTY TCNVDHKPSN TKVDKRVESK YGPPCPPCPA PEFEGGPSVF        240
LFPPKPKDTL MISRTPEVTC VVVDVSQEDP EVQFNWYVDG VEVHNAKTKP REEQFNSTYR        300
VVSVLTVLHQ DWLNGKEYKC KVSNKGLPSS IEKTISKAKG QPREPQVYTL PPSQEEMTKN        360
QVSLTCLVKG FYPSDIAVEW ESNGQPENNY KTTPPVLDSD GSFFLYSRLT VDKSRWQEGN        420
VFSCSVMHEA LHNHYTQKSL SLSLGKASQT PTNTISVTPT NNSTPTNNSN PKPNPASMHQ        480
KRTAMFQDPQ ERPRKLPQLC TELQTTIHDI ILECVYCKQQ LLRREVGDFA FRDLCIVYRD        540
GNPYAVCDKC LKFYSKISEY RHYCYSVYGT TLEQQYNKPL CDLLIRCINC QKPLCPEASM        600
HGDTPTLHEY MLDLQPETTD LYGYGQLNDS SEEEDEIDGP AGQAEPDRAH YNIVTFCCKA        660
SSSVSPTTSV HPTPTSVPPT PTKSSPAS                                          688

SEQ ID NO: 20           moltype = DNA  length = 2124
FEATURE                 Location/Qualifiers
source                  1..2124
                        mol_type = other DNA
                        organism = synthetic construct
SEQUENCE: 20
atgggttgga gcctcatctt gctcttcctt gtcgctgttg ctacgcgtgt ccactccgaa         60
gtgaagctgg tggagtctgg gggaggctta gtgcagccg agggtcccct gaaactctcc        120
tgtgcaacct ctggattcac tttcagtgac tattacatgt attgggttcg ccaggcccca       180
ggcaagggcc tggagtgggt cgcatacatt aattctggtg gtggtagcac ctattatcca       240
gacactgtaa agggccgatt caccatctcc agagacaatg ccaagaacac cctgtacctg       300
caaatgaaca gcctgagggc cgaggacaca gccgtgtatt actgtgcaag acggggggta       360
```

-continued

```
ccgttccatg ctatggacta ttggggtcaa ggaaccctgg tcaccgtctc ctcagccaaa    420
acgaagggcc catccgtctt cccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttccgcgctg tcctacagtc ctcaggactc    600
tactccctca gcagcgtggt gaccgtgccc tccagcagct tgggcacgaa gacctacacc    660
tgcaacgtag atcacaagcc cagcaacacc aaggtggaca gagagttga gtccaaatat    720
ggtcccccat gcccacccctg cccagcacct gagttcgaag ggggaccatc agtcttcctg    780
ttccccccaa aacccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caagggcag   1080
ccccgagagc cacaggtgta caccctgccc ccatcccagg aggagatgac caagaaccag   1140
gtcagcctga cctgcctggt caaaggcttc taccccagca catcgccgt ggagtgggag   1200
agcaatgggc agccggagaa caactacaag accacgcctc ccgtgctgga ctccgacggc   1260
tccttcttcc tctacagcag gctaaccgtg acaagagca ggtggcagga ggggaatgtc   1320
ttctcatgct ccgtgatgca tgaggctctg cacaaccact acacacagaa gagcctctcc   1380
ctgtctctgg gtaaagctag tcagacccccc accaacaca tcagcgtgac ccccaccaac   1440
aacagcaccc ccaccaacaa cagcaacccc aagcccaccc ccgctagtat gcaccaaaaaa   1500
aggaccgcaa tgtttcagga ccccaagag aggcccccgca aactgccaca actttgcacg   1560
gagctgcaga acaatataca tgacatcatt ctcgaatgtg tttactgtaa gcagcagttg   1620
ttgcgaagag aagtgggaga cttcgctttc agagacctgt gtatcgtata tcgcgatgc   1680
aatcctttatg ccgtctgcga taaatgcctc aagttttact ccaagatcag cgagtaccgg   1740
cactactgtt actctgtgta tgggactacc ctcgaacagc agtataacaa gccgctgtgc   1800
gatctcctta tccggtgcat taactgccag aagccactgt gtcctgaggc tagtatgcac   1860
ggggataccc ccacactcca cgaatacatg cttgatttgc aacctgaaac gaccgacctg   1920
tacgcctatg gtcagctgaa tgactccagc gaggaagagg atgagattga cggaccggca   1980
ggccaggccg agccagaccg ggctcattat aacatcgtga cttctgctg taaggctagt   2040
agcagcgtga gccccaccac cagcgtgcac cccacccccca ccagcgtgcc ccccaccccc   2100
accaagagca gccccgctag ctga                                         2124
```

```
SEQ ID NO: 21           moltype = AA   length = 689
FEATURE                 Location/Qualifiers
source                  1..689
                        mol_type = protein
                        organism = synthetic construct
SEQUENCE: 21
EVKLVESGGG LVQPGGSLKL SCATSGFTFS DYYMYWVRQA PGKGLEWVAY INSGGGSTYY     60
PDTVKGRFTI SRDNAKNTLY LQMNSLRAED TAVYYCARRG LPFHAMDYWG QGTLVTVSSA    120
KTKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVMHEA LHNHYTQKSL SLSLGKASQT PTNTISVTPT NNSTPTNNSN PKPNPASMAR    480
FEDPTRRPYK LPDLCTELNT SLQDIEITCV YCKTVLELTE VGEFAFKDLF VVYRDSIPHA    540
ACHKCIDFYS RIRELRHYSD SVYGDTLEKL TNTGLYNLLI RCLRCQKPLN PASMHGPKAT    600
LQDIVLHLEP QNEIPVDLLG HGQLSDSEEE NDEIDGVNHQ HLPARRAEPQ RHTMLCMCCK    660
ASSSVSPTTS VHPTPTSVPP TPTKSSPAS                                    689
```

```
SEQ ID NO: 22           moltype = DNA   length = 2127
FEATURE                 Location/Qualifiers
source                  1..2127
                        mol_type = other DNA
                        organism = synthetic construct
SEQUENCE: 22
atgggttgga gcctcatctt gctcttcctt gtcgctgttg ctacgcgtgt ccactccgaa     60
gtgaagctgt ggagtctggg ggaggcttag tgcagcccg agggtccct gaaactctcc    120
tgtgcaacct ctggattcac tttcagtgac tattacatgt attgggttcg ccaggcccca    180
ggcaagggcc tggagtgggt cgcatacatt aattctgtg gtggtagcac ctattatcca    240
gacactgtaa agggccgatt caccatctcc agagacaatg ccaagaacac cctgtacctg    300
caaatgaaca gcctgagggc cgaggacaca gccgtgtatt actgtgcaag acgggggtta    360
ccgttccatg ctatggacta ttggggtcaa ggaaccctgg tcaccgtctc ctcagccaaa    420
acgaagggcc catccgtctt cccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttccgcgctg tcctacagtc ctcaggactc    600
tactccctca gcagcgtggt gaccgtgccc tccagcagct tgggcacgaa gacctacacc    660
tgcaacgtag atcacaagcc cagcaacacc aaggtggaca gagagttga gtccaaatat    720
ggtcccccat gcccacccctg cccagcacct gagttcgaag ggggaccatc agtcttcctg    780
ttccccccaa aacccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caagggcag   1080
ccccgagagc cacaggtgta caccctgccc ccatcccagg aggagatgac caagaaccag   1140
gtcagcctga cctgcctggt caaaggcttc taccccagca catcgccgt ggagtgggag   1200
agcaatgggc agccggagaa caactacaag accacgcctc ccgtgctgga ctccgacggc   1260
tccttcttcc tctacagcag gctaaccgtg acaagagca ggtggcagga ggggaatgtc   1320
ttctcatgct ccgtgatgca tgaggctctg cacaaccact acacacagaa gagcctctcc   1380
```

```
ctgtctctgg gtaaagctag tcagaccccc accaacacca tcagcgtgac ccccaccaac   1440
aacagcaccc ccaccaacaa cagcaacccc aagcccaacc ccgctagtat ggccagattc   1500
gaggatccaa cacgccgacc ttacaaattg ccggaccttt gcacggagct gaacacttcc   1560
ctgcaggaca tagaaattac ctgcgtctac tgcaagaccg ttctcgaact gacagaagta   1620
ggcgagtttg cgtttaaaga tctgttcgtg gtgtatcgga atagcattcc ccacgcagct   1680
tgtcataagt gtatcgactt ctattctagg atccgggagc tcagacacta tagcgattcc   1740
gtgtacggcg acacacttga gaagctcact aacaccgggc tgtacaacct cctgatccgg   1800
tgcttgaggt gtcagaaacc cctgaatcct gctagtatgc acgggcctaa ggccacactg   1860
caagatattg tcctccatct cgaacccccag aatgagatac cagtggacct tctgggccac   1920
ggacagttgt ccgatagcga ggaggaaaac gacgaaatcg acggtgttaa ccaccagcac   1980
ttgccggctc ggagggcaga gccccagaga cataccatgc tgtgcatgtg ttgcaaagct   2040
agtagcagcg tgagcccac caccagcgtg caccccaccc ccaccagcgt gccccccacc   2100
cccaccaaga gcagccccgc tagctga                                       2127

SEQ ID NO: 23           moltype = AA  length = 242
FEATURE                 Location/Qualifiers
source                  1..242
                        mol_type = protein
                        organism = synthetic construct
SEQUENCE: 23
MKKLLIAAMM AAALAACSQE AKQEVKEAVQ AVESDVKDTA MGSSHHHHHH SSGLVPRGSH    60
MASMDLDAVR IKVDTVNAKP GDTVNIPVRF SGIPSKGIAN CDFVYSYDPN VLEIIEIKPG   120
ELIVDPNPTK SFDTAVYPDR KMIVPLFAED SGTGAYAITK DGVFATIVAK VKEGAPNGLS   180
VIKFVEVGGF ANNDLVEQKT QFFDGGVNVG DTTEPATPTT PVTTPTTTDD LDAASLIKTS   240
EF                                                                 242

SEQ ID NO: 24           moltype = DNA  length = 729
FEATURE                 Location/Qualifiers
source                  1..729
                        mol_type = other DNA
                        organism = synthetic construct
SEQUENCE: 24
atgaaaaaac tgctgattgc cgccatgatg gctgcagctc tggccgcatg cagccaggaa    60
gccaaacagg aagtgaaaga agccgtgcag gccgtggaag cgatgtgcga agataccgct   120
atgggcagca gccatcatca tcatcatcac agcagcggcc tggtgccgcg cggcagccat   180
atggctagta tggatctgga tgcagtaagg attaaagtgg acacagtaaa tgcaaaaccg   240
ggagacacag taaatatacc tgtaagattc agtggatacc atccaagggg aatagcaaac   300
tgtgactttg tatacagcta tgacccgaat gtacttgaga taatagatat aaaaccggga   360
gaattgatag ttgacccgaa tcctaccaag agctttgata ctgcagtata tcctgacgaa   420
aagatgatag tattcctgtt tgcggaagac agcggaacag gagcgtatgc aataactaaa   480
gacggagtat ttgctacgat agtagcgaaa gtaaaagaag gagcacctaa cgggctcagt   540
gtaatcaaat ttgtagaagt aggcggattt gcgaacaatg accttgtaga acagaagaca   600
cagttctttg acggtggagt aaatgttgga gatacaacag aacctgcaac acctacaaca   660
cctgtaacaa caccgacaac aacagatgat ctagatgcag ctagcttaat taaaactagt   720
gaattctga                                                          729

SEQ ID NO: 25           moltype = AA  length = 448
FEATURE                 Location/Qualifiers
source                  1..448
                        mol_type = protein
                        organism = synthetic construct
SEQUENCE: 25
DIQMTQSPSS LSASVGDRVT ITCSASQGIS NYLNWYQQKP GKAVKLLIYY TSILHSGVPS    60
RFSGSGSGTD YTLTISSLQP EDFATYYCQQ FNKLPPTFGG GTKLEIKRTV AAPSVFIFPP   120
SDEQLKSGTA SVVCLLNNFY PREAKVQWKV DNALQSGSNQ STVEQDSKD STYSLSSTLT   180
LSKADYEKHK VYACEVTHQG LSSPVTKSFN RGECASIERL SSGLRINSAK DDAAGQAIAN   240
RPFTANIKGLT QASRNANDGI SIAQTTEGAL NEINNNLQRV RELAVQSANS TNSQSDLDSI   300
QAEITQRLNE IDRVSGQTQF NGVKVLAQDN TLTIQVGAND GETIDIDLKQ INSQTLGLDS   360
LNVQASQPEL AEAAAKTTEN PLQKIDAALA QVDALRSDLG AVQNRFNSAI TNLGNTVNNL   420
SEARSRIEDS DYATEVSNMS RAQILQAS                                     448

SEQ ID NO: 26           moltype = DNA  length = 1407
FEATURE                 Location/Qualifiers
source                  1..1407
                        mol_type = other DNA
                        organism = synthetic construct
SEQUENCE: 26
atgagggtcc ccgctcagct cctggggctc ctgctgctct ggctcccagg cgcgcgatgt    60
gatatccaga tgacacagag ccccttcctc ctgtctgcct ctgtgggaga cagagtcacc   120
atcacctgca gtgcaagtca gggcattagc aattatttaa actggtatca gcagaaacca   180
ggcaaggccg ttaaactcct gatctattac acatcaattt tacactcagg agtcccatca   240
aggttcagtg gcagtgggtc tgggacagat tataccctca ccatcagctc cctgcagcct   300
gaagatttcg ccacttacta ttgtcagcag tttaataagc ttcctccgac gttcggtgga   360
ggcaccaaac tcgagatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctatgcct gcgaagtcac ccatcagggc   660
ctgagctcgc ccgtcacaaa gagcttcaac aggggagagt gtgctagtat cgagcgtctg   720
```

-continued

```
cttctggtc tgcgtatcaa cagcgcgaaa gacgatgcgg caggtcaggc gattgctaac    780
cgttttaccg cgaacatcaa aggtctgact caggcttccc gtaacgctaa cgacggtatc    840
tccatcgcgc agaccactga aggcgcgctg aacgaaatca caacaacct gcagcgtgtg     900
cgtgaactgc cggttcagtc tgctaacagc actaactccc agtctgacct cgactccatc    960
caggctgaaa tcacccagcg cctgaacgaa atcgaccgtg tatccggtca gactcagttc   1020
aacggcgtga agtcctggc gcaggacaac ccctgacca tccaggttgg tgccaacgac     1080
ggtgaaacta tcgatatcga tctgaagcag atcaactctc agaccctggg cctggattca   1140
ctgaacgtgc aggctagtca accagagctg gcggaagcag ccgctaaaac caccgaaaac   1200
ccgctgcaga aaattgatgc cgcgctggcg caggtggatg cgctcgctc tgatctgggt    1260
gcggtacaaa accgtttcaa ctccgctatc accaacttgg gcaataccgt aaacaacctg   1320
tctgaagcgc gtagccgtat cgaagattcc gactacgcga ccgaagtttc caacatgtct   1380
cgcgcgcaga ttctgcaggc tagctga                                       1407
```

SEQ ID NO: 27          moltype = AA    length = 658
FEATURE                Location/Qualifiers
source                 1..658
                       mol_type = protein
                       organism = synthetic construct
SEQUENCE: 27
QVQLRQSGPE LVKPGASVKM SCKASGYTFT DYVISWVKQR TGQGLEWIGD IYPGSGYSFY     60
NENFKGKATL TADKSSTTAY MQLSSLTSED SAVYFCATYY NYPFAYWGQG TLVTVSAAKT    120
TGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FEGGPSVFLF    240
PPKPKDTLMI SRTPEVTCVV VDVSQEDPEV QFNWYVDGVE VHNAKTKPRE EQFNSTYRVV    300
SVLTVLHQDW LNGKEYKCKV SNKGLPSSIE KTISKAKGQP REPQVYTLPP SQEEMTKNQV    360
SLTCLVKGFY PSDIAVEWES NGQPENNYKT TPPVLDSDGS FFLYSRLTVD KSRWQEGNVF    420
SCSVMHEALH NHYTQKSLSL SLGKASMHGP KATLQDIVLH LEPQNEIPVD LLGHGQLSDS    480
EEENDEIDGV NHQHLPARRA EPQRHTMLCM CCKASMARFE DPTRRPYKLP DLCTELNTSL    540
QDIEITCVYC KTVLELTEVG EFAFKDLFVV YRDSIPHAAC HKCIDFYSRI RELRHYSDSV    600
YGDTLEKLTN TGLYNLLIRC LRCQKPLNPA SSSVSPTTSV HPTPTSVPPT PTKSSPAS     658

SEQ ID NO: 28          moltype = DNA    length = 2031
FEATURE                Location/Qualifiers
source                 1..2031
                       mol_type = other DNA
                       organism = synthetic construct
SEQUENCE: 28
atggaatgga ggatctttct cttcatcctg tcaggaactg caggtgtcca ctcccaggtt     60
cagctgcggc agtctggacc tgagctggtg aagcctggag cttcagtgaa gatgtcctgc    120
aaggcttctg gatacacatt tactgactat gttataagtt gggtgaagca gagaactgga    180
cagggccttg agtggattgg agatatttat cctggaagtg gttattcttt ctacaatgag    240
aacttcaagg gcaaggccac actgactgca gacaaatcct ccaccacagc ctacatgcag    300
ctcagcagcc tgacatctga ggactctgcg gtctatttct gtgcaacta ctataactac    360
ccttttgctt actggggcca agggactctg gtcactgtct ctgcagccaa acaacgggc    420
ccatccgtct tccccctggc gccctgctcc aggagcacct ccgagagcac agccgccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcacga gacctacac ctgcaacgta    660
gatcacaagc ccagcaacac caaggtggac aagagagttg agtccaaata tggtccccca    720
tgcccaccct gcccagcacc tgagttcgaa ggggaccat cagtcttcct gttcccccca    780
aaaccccaagg acactctcat gatctcccgg acccctgagg tcacgtgcgt ggtggtggac    840
gtgagccagg aagacccga ggtccagttc aactggtacg tggatggcgt ggaggtgcat    900
aatgccaaga caaagccgcg ggaggagcag ttcaacagca cgtaccgtgt ggtcagcgtc    960
ctcaccgtcc tgcaccagga ctggctgaac ggcaaggagt acaagtgcaa ggtctccaac   1020
aaaggcctcc cgtcctccat cgagaaaacc atctccaaag ccaaagggca gccccgagag   1080
ccacaggtgt acaccctgcc cccatcccag gaggagatga ccaagaacca ggtcagcctg   1140
acctgcctgg tcaaaggctt ctaccccagc gacatcgccg tggagtggga gagcaatggg   1200
cagccggaga caactacaa gaccacgcct ccgtgctgg actccgacgg ctccttcttc   1260
ctctacagca ggctaaccgt ggacaagagc aggtggcagg aggggaatgt cttctcatgc   1320
tccgtgatgc atgaggctct gcacaaccac tacacacaga gagcctctc cctgtctctg   1380
ggtaaagcta gtatgcacgg gcctaaggcc acactgcaag atattgtcct ccatctcgaa   1440
ccccagaatg agataccagt ggaccttctg gccacggac agttgtccga tagcgaggag   1500
gaaaacgacg aaatcgacgg tgttaaccac cagcacttgc cggctcggag ggcagagccc   1560
cagagacata ccatgctgtg catgtgttgc aaagctgta tggccagatt cgaggatcca   1620
acacgccgac cttacaaatt gccgaccctt tgcacggagc tgaacacttc cctgcaggac   1680
atagaaatta cctgcgtcta ctgcaagacc gttctcgaac tgacagaagt aggcgagttt   1740
gcgtttaaag atctgttcgt ggtgtatcgg gatagcattc cccacgcagc ttgtcataag   1800
tgtatcgact tctattctag gatccgggag ctcagacact atagcgattc cgtgtacggc   1860
gacacacttg agaagctcac taacaccggg ctgtacaacc tcctgatccg gtgcttgagg   1920
tgtcagaaac ccctgaatcc tgctagtagc agcgtgagcc ccaccaccag cgtgcacccc   1980
acccccacca gcgtgccccc caccccccacc aagagcagcc ccgctagctg a           2031

SEQ ID NO: 29          moltype = AA    length = 25
FEATURE                Location/Qualifiers
source                 1..25
                       mol_type = protein
                       organism = synthetic construct
SEQUENCE: 29
PTSTPADSST ITPTATPTAT PTIKG                                           25

```
SEQ ID NO: 30          moltype = AA  length = 25
FEATURE                Location/Qualifiers
source                 1..25
                       mol_type = protein
                       organism = synthetic construct
SEQUENCE: 30
TVTPTATATP SAIVTTITPT ATTKP                                              25

SEQ ID NO: 31          moltype = AA  length = 25
FEATURE                Location/Qualifiers
source                 1..25
                       mol_type = protein
                       organism = synthetic construct
SEQUENCE: 31
TNGSITVAAT APTVTPTVNA TPSAA                                              25
```